US011583518B2

(12) United States Patent
El Glaoui et al.

(10) Patent No.: US 11,583,518 B2
(45) Date of Patent: *Feb. 21, 2023

(54) NON-HORMONAL COMPOSITIONS AND METHODS FOR MALE CONTRACEPTION

(71) Applicant: PHARMAJOR INTERNATIONAL, Luxembourg (LU)

(72) Inventors: Guillaume El Glaoui, Luxembourg (LU); Mehdi El Glaoui, Luxembourg (LU); Philippe Perrin, Paris (FR); Stéphane Droupy, Nimes (FR); Véronique Agathon-Meriau, Luxembourg (LU)

(73) Assignee: PHARMAJOR INTERNATIONAL, Luxembourg (LU)

( * ) Notice: Subject to any disclaimer, the term of this patent is extended or adjusted under 35 U.S.C. 154(b) by 152 days.

This patent is subject to a terminal disclaimer.

(21) Appl. No.: 17/137,747

(22) Filed: Dec. 30, 2020

(65) Prior Publication Data

US 2021/0113526 A1   Apr. 22, 2021

Related U.S. Application Data

(63) Continuation of application No. 16/362,081, filed on Mar. 22, 2019, now Pat. No. 10,912,762.

(60) Provisional application No. 62/763,129, filed on Mar. 23, 2018.

(30) Foreign Application Priority Data

Mar. 23, 2018 (EP) ..................... 18305328

(51) Int. Cl.
*A61K 31/4045* (2006.01)
*A61P 15/16* (2006.01)
*A61K 9/16* (2006.01)
*A61K 9/00* (2006.01)
*A61K 9/50* (2006.01)
*A61K 45/06* (2006.01)

(52) U.S. Cl.
CPC ........ *A61K 31/4045* (2013.01); *A61K 9/0053* (2013.01); *A61K 9/16* (2013.01); *A61K 9/5078* (2013.01); *A61P 15/16* (2018.01); *A61K 45/06* (2013.01)

(58) Field of Classification Search
CPC .................................................. A61K 31/4045
See application file for complete search history.

(56) References Cited

U.S. PATENT DOCUMENTS

| 4,210,644 | A | 7/1980 | Ewing et al. | |
| 10,912,762 | B2 * | 2/2021 | El Glaoui | A61K 9/16 |
| 2008/0031946 | A1 | 2/2008 | Tchoreloff et al. | |
| 2008/0242717 | A1 | 10/2008 | Sato et al. | |
| 2009/0186896 | A1 | 7/2009 | Ulbrich et al. | |
| 2012/0184591 | A1 | 7/2012 | Hoel et al. | |
| 2017/0049834 | A1 | 2/2017 | Liu | |

FOREIGN PATENT DOCUMENTS

| CN | 102283816 A | 12/2011 |
| EP | 1267885 B1 | 1/2003 |
| RU | 2122854 C1 | 12/1998 |
| WO | 2008087421 A3 | 7/2008 |
| WO | 2014118606 A2 | 8/2014 |

OTHER PUBLICATIONS

Akin et al. "Comparison of Alpha Blockers in Treatment of Premature Ejaculation: A Plot Clinical Trial" Iranian Red Crescent Medical Journal 15(10) 1-6 (2013).
Akiyama et al. "Relationship between Prostative a1-Adrenoceptor Binding and Reduction in Intraurethral Pressure following Continuous Infusion of KMD-3213 in Rats" Pharmacology 64 140-147 (2002).
Behre et al. "Efficacy and Safety of an Injectable Combination Hormonal Contraceptive for Men" J Clin Endocrinol Metab 101(12) 4779-4788 (2016).
Benson et al. Treatment of the signs and symptoms of benign prostatic hyperplasia. Center for Drug Evaluation and Research1-220 (2008).
Bhat et al. "BKP 02: Prospective double blind randomized study to evaluate the efficacy of Silodosin 8 mg as on demand, reversible, male oral contraceptive" Indian J Urology 34(5 Suppl. 1): p. S7 (2018).
Bhat et al. "Effectiveness of 'on demand' silodosin in the treatment of premature ejaculation in patients dissatisfied with dapoxetine: a randomized control study" Cent European J Urol 69 280-284 (2016).
Bozkurt et al. "Silodosin causes impaired ejaculation and enlargement of seminal vesicles in sexually active men treated for lower urinary tract symptoms suggestive of benign prostatic hyperplasia" Male Sexual Dysfunction Urology 85(5) 1085-1089 (2015).
Capogrosso et al., "Effects of silodosin on sexual function—realistic picture from the everyday clinical practice" Andrology 3 1076-1081 (2015).

(Continued)

Primary Examiner — Svetlana M Ivanova
(74) Attorney, Agent, or Firm — Nixon Peabody LLP; Mark J. FitzGerald

(57) ABSTRACT

The present invention relates to non-hormonal compositions and methods for inducing a condition of aspermia, azoospermia, or severe oligozoospermia in the male subject such that these compositions and methods for administering the same may be used as male contraception. Embodiments of the present invention may comprise a composition comprising an alpha-1-adrenoreceptor antagonist, such as (R)-silodosin, for daily administration to a male subject. The compositions and related methods may further include pharmaceutically acceptable carriers. The present invention further includes formulations which allow for a delay such that delayed or missed dose(s) do not nullify the contraceptive effect of the treatment regimen. Such compositions and methods may also avoid the side effects associated with typical formulations of alpha-1-adrenoreceptor antagonists.

16 Claims, 2 Drawing Sheets

(56) References Cited

OTHER PUBLICATIONS

Chapple et al. "Silodosin Therapy for Lower Urinary Tract Symptoms in Men with Suspected Benign Prostatic Hyperplasia: Results of an International, Randomized, Double-Blind, Placebo- and Active-Controlled Clinical Trial Performed in Europe" European Urology 59 342-352 (2011).
Chen et al. "Blockade of a1A-Adrenoceptor: A novel possible strategy for male contraception" Medical Hypotheses 73 140-141 (2009).
Coolen et al. "Central regulation of ejaculation" Physiology & Behavior 83 203-215 (2004).
Guerin et al. "Inhibition of spermatogenesis in men using various combinations of oral progestagen and percutaneous or oral androgens" International Journal of Andrology 11 187-199 (1988).
Hancock et al., "Preclinical Pharmacology of Fiduxosin, a Novel a1-Adrenoceptor Antagonist with Uroselective Properties" The Journal of Pharmacology and Experimental Therapeutics 300(2) 478-486 (2001).
Hayashi et al. "Effects of Silodosin and Tamsulosin on the Seminal Vesicle Contractile Response" LUTS 8 55-61 (2016).
Hellstrom et al. "Effects of Acute Treatment With Tamsulosin Versus Alfuzosin on Ejaculatory Function in Normal Volunteers" The Journal of Urology 176 1529-1533 (2006).
Hellstrom et al. "Effects of Alfuzosin and Tamsulosin on Sperm Parameters in Healthy Men: Results of a Short-Term, Randomized, Double-Bling, Placebo-Controlled, Crossover Study" J Androl 30(4) 469-474 (2009).
Hemmings et al. CHMP Assessment Report for Urorec international Nonproprietary Name: silodosin European Medicines Agency 1-60 (2010).
Hisasue et al. "Ejaculatory disorder caused by aipha-1 andrenoceptor antagonists in not retrograde ejaculation but a loss of seminal emission" International Journal of Urology 13 1311-1316 (2006).
Homma et al. "Ejacluation Disorder is Associated With Increased Efficacy of Silodosin for Benign Prostatic Hyperplasia" J Urology 76(6) 1446-1450 (2010).
Homonnai et al. "Phenoxybenzamine—An Effectice Male Contraceptive Pill" Contraception Soferman Institute for the Study of Fertility 29(5) 479-491 (1984).
Huang et al. "Phosphodiesterase-5 (PDE5) Inhibitors In the Management of Erectile Dysfunction" Pharmacy and Therapeutics 38(7) 407 & 414-419 (2013).
Kamischke et al. "Intramuscular Testosterone Undecanoate and Norethisterone Enanthate in a Clinical Trail for Male Contraception" Institute of Reproductive Medicine 86(1) 303-309 (2000).
Kawabe et al. "Silodosin, a new a1A-adrenoceptor-selective antagonist for treating benign prostatic hyperplasia results of a phase III randomized, placebo-controlled, double-blind study in Japanese men" Journal Compilation BJU International 98 1019-1024 (2006).
Kjaergaard et al. "Prazosin, an Adrenergic Blocking Agent Inadequate as Male Contraceptive Pill" Contraception 37(6) 621-629 (1988).
Kobayashi et al. "Inhibition of Seminal emission is the main cause of anejaculation induced by a new highly selective 1A-blocker in normal volunteers" J Sex Med 5 2185-2190 (2008).
Kobayashi et al. "Orgasm is preserved regardless of ejaculatory dysfunction with selective 1A-Blocker administration" International Journal of Impotence Research 21 306-310 (2009).
Kobayashi et al. "Orgasm is Preserved Regardless of Ejaculatory Dysfunction with Selective Aipha-1A-Blocker Administration" Eur Urol Suppl 7(3) 461-464 (2008).
Manjunatha et al. "A randomized comparative, open-label study of efficacy and tolderability of alfuzosin, tamsulosin and silodosin in benign prostatic hyperplasia" Indian J Pharacol. 48(2) 1-15 (2016).
Marks et al. "Silodosin in the Treatment of the Signs and Symptoms of Benign Prostatic Hyperplasia: A 9-Month, Open-label Exlension Study" J Urology 74(6) 1318-1324 (2009).

McLeod-Flynn Pharmacology/Toxicology review and evaluation for Silodosin Department of Health and Human Services Food and Drug Administration 1-180 (2007).
Meriggiola et al. "Low dose of cyproterone acetate and testosterone enanthate for contraception in men" Human Reproduction 13(5) 1225-1229 (1998).
Miyakita et al. "Short-term effects of crossover treatment with silodosin and tamsulosin hydrochloride for lower urinary tract symptoms associated with benign prostatic hyperplasia" International Journal of Urology 17 869-875 K2010).
Montorsi et al. "Effectiveness and safety of silodosin in the treatment of lower urinary tract symptoms in patients with benign prostatic hyperplasia: A European phase IV clinical study (SIRE study)" International Journal of Urology 23 572-579 (2016).
Moon et al. "Efficacy and Safety of the Selective a1A-Adrenoceptor Blocker Silodosin for Severe Lower Urinary Tract Symptoms Associated 'With Benign Prostatic Hyperplasia: A Prospective, Singie-Open-Label, Multicenter Study in Korea" Korean J Urol 55 335-340 (2014).
Moriyama et al. "KMD-3213, a novel a1A-adrenoceptor antagonist, potently inhibits the functional a1-andrenoceptor in human prostate" European Journal of Pharmacology 337 39-42 (1997).
Nagai et al. "Ejaculatory dysfunction caused by the new a 1-blocker silodosin: A preliminary study to analyze human ejaculation using color Doppler ultrasonography" International Journal of Urology 15 915-918 (2008).
Nieschlag et al. "Testosterone in male contraception" Testosterone Chapter 18 513-528 (1998).
Nokhodchi et al. "The Role of Oral Controlled Release Matrix Tablets in Drug Delivery Systems" Bioimpacts 2(4) 175-187 (2012).
Osman et al. "Open-label, 9-month extension study investigating the uro-selective alpha-blocker silodosin in men with LUTS associated with BPH" World J Urol 33 697-706 (2015).
Patrao et al. "Cloning, expression and immunolocaiization of a1-adrenoceptor in different tissues from rhesus monkey and human male reproductive tract", MHR-Basic Science of Reproductive Medicine 14(2) 85-96 (2008).
RECORDATI Ireland Limited Summary of Product Characteristics for Urorec 8 mg capsules Medicines.ie 1-18 (2005).
Roehrborn et al. "a1-Blockers in Men with Lower Urinary Tract Symptoms Suggestive of Benign Prostatic Obstruction: Is Silodosin Different?" Adv Ther 33 2110-2121 (2016).
Rosenberg et al. "Compliance, Counseling and Satisfaction with Oral Contraceptives: A Prospective Evaluation" Family Planning Perspectives 30(2) 89-92 & 104 (1998).
Rumondor et al. "Minitablets: Manufacturing, Characterization Methods, and Future Opportunities" American Pharmaceutical Review 1-11 https://www.americanpharmaceuticalreview.com/Featured-Articles/190921-Minitablets-Manufacturing-Characterization-Methods-and-Future-Opportunities/ (2016).
Sakata et al. "Investigation of ejaculatory disorder by silodosin in the treatment of prostatic hyperplasia" BMC Urology 12(29) 1-6 (2012).
Sanbe et al. "a1-Adrenoceptors are required for normal male sexual function" British Journal of Pharmacology 152 332-340 (2007).
Sato et al. "Silodosin and its potential for treating premature ejaculation: A preliminary report" International Journal of Urology 19 268-272 (2012).
Schwartz et al. "Drug Interactions with Phosphodiesterase-5 Inhibitors Used for the Treatment of Erectile Dysfunction or Pulmonary Hypertension" Circulation 122 88-95 (2010).
Shimizu et al. "impact of dry ejaculation caused by highly selective 1A-blocker: randomized, double-blind, placebo-controlled crossover pilor study in healthy volunteer men" J Sex Med 7 1277-1283 (2010).
Sung et al. "New Methodology for Investigating Ejaculation Dysfunction: Measuring Intraluminal Seminal Vesicle Pressure in Rats with a Telemetric Device" J Sex Med 12 2134-2140 (2015).
Takao et al. "Early efficacy of silodosin in patients with lower urinary tract symptoms suggestive of benign prostatic hyperplasia" International Journal of Urology 15 992-996 (2008).

(56) References Cited

OTHER PUBLICATIONS

Tatemichi et al. "Comparison of the Effects of Four a1-Adrenoceptor Antagonists on Ejaculatory Function in Rats" Urology 80(2) 486.e9-486.e16 (2012).

Tatemichi et al. "Uroselectivity in Male Dogs of Silodosin (KMD-3213), A Novel Drug for the Obstructive Component of Benign Prostatic Hyperplasia" Neurology and Urodynamics 25 792-799 (2006).

Timmins et al. "Hydrophilic matrix dosage forms: Definitions, general attributes, and the evolution of clinical utilization" Chapter 1 Hydrophilic Matrix Tablet for Oral Controlled Release 1-15 (2014).

Tran et al. Clinical Pharmacology and Biopharmaceutics Review(s) for Silodosin. Center for Drug Evaluation and Research Office of Clinical Pharmacology Review 1-86 (2008).

Turner et al. "Contraceptive Efficacy of a Depot Progestin and Androgen Combination in Men" J Clin Endocrinol 88 (10) 4659-4667 (2003).

Wang et al. "Assessment of Tamsulosin as a Potential Male Contraceptive in Healthy Volunteers" Male Sexual Dysfunction Urology 80(3) 614-617 (2012).

White et al. "Male contraception via simultaneous knockout of a1A-adrenoceptors and P2X1-purinoceptors in mice" PNAS 110(51) 20825-20830 (2013).

World Health Organization "Contraceptive efficacy of testosterone-induced azoospermia and oliozoospermia in normal men" Fertility and Sterility Urology-andrology 65(4) 821-829 (1996).

Yokoyama et al. "Effects of three types of alpha-1 adrenoceptor blocker on lower urinary tract symptoms and sexual function in males with benign prostatic hyperplasia" International Journal of Urology 18 225-230 (2011).

Yono et al. "Short- and long-term effects of silodosin, and selective a1A-adrenoceptor antagonist, on ejaculatory function in rats" Journal Compilation BJU International 103 1680-1685 (2009).

Yu et al. "Non-inferiority of silodosin to tamsulosin in treating patients with lower urinary tract symptoms (LUTS) associated with benign prostatic hyperplasia (BPH)" BJU International 103 1843-1848 (2011).

PCT/EP2019/057567 International Search Report dated May 24, 2019, 4 pgs.

* cited by examiner

NON-HORMONAL COMPOSITIONS AND METHODS FOR MALE CONTRACEPTION

CROSS REFERENCE TO RELATED APPLICATIONS

This application is a continuation application under 35 U.S.C. § 120 of co-pending U.S. application Ser. No. 16/362,081 filed Mar. 22, 2019, which claims benefit under 35 U.S.C. § 119(e) of U.S. Provisional Application No. 62/763,129 filed Mar. 23, 2018, and EP 18305328.9 filed Mar. 23, 2018, the contents of which are incorporated herein by reference in their entirety.

INCLUSION OF COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to non-hormonal compositions and methods for male contraception in order to prevent pregnancy in female sexual partners.

BACKGROUND

Although pharmaceutical compositions and methods for female contraception have been well known in the art for decades, the same cannot be said for male contraception. The high demand for such a product is based upon the individual needs of each male subject, and may include, for example, the desire or need to reduce the burden of oral hormonal contraception on any female partner, or to minimize the possibility of failures associated with female contraception. Notwithstanding this demand, development of contraceptive pharmaceutical compositions and methods for men has proven to be a major medical challenge.

Currently, the majority of available contraception methods are female contraceptives. Few options exist for men wishing to assume the birth control responsibility, which amount mainly to the use of prophylactics, such as condoms. The numerous draw-backs of condoms are well known in the field, and include both potential for failure (i.e., breaking or improper use) as well as a decrease in sexual sensation. Another contraceptive option available to men is the surgical option of having a vasectomy, a procedure in which the male vas deferens are severed and then tied or sealed in a manner so as to prevent sperm from entering into the urethra. A vasectomy is typically considered to be a permanent method of sterilization, and is not easily reversed, and so is not a viable option for any male subject who wishes to have children at any point in the future.

In light of this, efforts have been made to find a safe, effective, hormone-based, or chemical-based reversible contraceptive for males. Historically, most therapeutic targets have been hormonal and therefore likely to have intolerable sexual, behavioral, physiological, and psychological side effects, such as loss of sexual desire, loss of virility (e.g. erectile dysfunction, breast tenderness and growth of breast tissue, shrinkage of testicles and penis or loss of muscle mass), depression, possible suicidal thoughts, decreased mental sharpness, weight gain, fatigue or hot flashes. Nieschlag et al. discloses that hormonal methods of male contraception offer the advantages of high-reversibility and efficacy. In male hormonal contraception, the suppression of spermatogenesis is sought through the suppression of the gonadotropins luteinizing hormone (LH) and follicle stimulating hormone (FSH) to undetectable levels within the endocrine feedback mechanism operating between the pituitary gland and the hypothalamus. Disadvantageously, suppression of these gonadotropins also induces symptoms related to androgen deficiency (Nieschlag et al., Testosterone: Action, Deficiency, Substitution, Springer-Verlag, 1998, 513-528). Thus male contraceptive methods seeking to suppress FSH and LH may result in a depletion of intratesticular testosterone and cessation of spermatogenesis, whilst substituting peripheral testosterone with another androgen. The substitute androgen typically is testosterone itself.

The male urinary smooth muscles contain high densities of alpha-1-adrenoceptors and several alpha-1-adrenoceptor subtypes have been identified, namely alpha-1a, alpha-1b and alpha-1 d-adrenoceptor subtypes. The alpha-1a-adrenoceptor subtype has been described to be predominant in the human prostate and is present in the male reproductive tract tissues (testis, epididymis, seminal vesicle and prostate) (Patrão et al, MHR-BASIC SCIENCE OF REPRODUCTIVE MEDICINE, 2008, 14 (2), 85-96).

Hormonal contraceptive methods have other drawbacks as well, including, for example, the requirement of high dosage amounts (Guerin et al, INTERNATIONAL JOURNAL OF ANDROLOGY, 1988, 11 (3), 187-199) and frequent injection schedules (World Health Organization Task Force on Methods for the Regulation of Male Fertility, FERTIL. STERIL., 1996, 65(4), 821-829 ("WHO Task Force 1996").

Meriggiola et al. describe the association of testosterone enanthate (100 mg/week by intramuscular route) and the progestins cyproterone acetate (112.5 or 25 mg/day by oral route). The low dose regimen was ineffective in the suppression of spermatogenesis and the high dose regimen led to significant decreases in hemoglobin and hematocrit (indicative of red blood cell count?), as shown in Meriggiola et al., HUMAN REPRODUCTION, (1998) 13(5) 1225-1229.

U.S. Pat. No. 4,210,644 discloses the simultaneous use of an androgen and an estrogen, both compounds being separately implanted subcutaneously in two distinct slow release capsules. Reversible male infertility is observed in rats but no data in humans are provided.

Guerin et al. disclose a method inhibiting spermatogenesis in men comprising the step of administering testosterone percutaneously or orally and the progestin norethisterone acetate orally. Guerin et al., INT'L J. ANDROLOGY, (1988), 11 (3) 187-199. However, high doses of each component were required to achieve azoospermia and several female partners had elevated plasma levels of testosterone. In addition, two among twelve subjects exhibited a partial restoration of sperm count.

The World Health Organization published the results of a large multicenter contraceptive study in which healthy men received 200 mg testosterone enanthate weekly by intramuscular injection for 6 months. The low pregnancy rates were promising, but the frequent injection schedule was a problem. WHO Task Force 1996.

EP 1 267 885 discloses the use of norethisterone derivative possessing both androgenic and estrogenic properties in combination with a testosterone ester in a non-oral formulation. The formulation comprising norethisterone enanthate and testosterone undecanoate, is administered by intramuscular injection every 6 weeks to maintain the contraceptive effect.

In a clinical trial conducted with a norethisterone enanthate (1000 mg)-testosterone undecanoate (200 mg) intramuscular formulation, Kamischke A. et al demonstrated that the highest azoospermia rate was achieved 8 weeks after the end of the 24-week treatment period (Kamischke A. et al., J. CLIN. ENDOCRINOL. METAB., (2001). 86(1), 303-309).

A further multicenter study in which patients received intramuscular injections of 200-mg norethisterone enanthate combined with 1000-mg testosterone undecanoate, administered every 8 weeks showed that the study regimen led to near-complete and reversible suppression of spermatogenesis. The contraceptive efficacy was relatively good compared with other reversible methods available for men but the study was prematurely stopped because of adverse events (mood disorders, pain at the injection site and increased libido). Behre H M et al. J Clin Endocrinol Metab (2016) 101:4779-4788.

Turner L et al. disclose a hormonal male contraception using four 200-mg (ie, 800 mg) intramuscular implants of testosterone administered every 6 or 4 months and one 300-mg medoxyprogesterone acetate subcutaneous depot administered every 4 or 3 months. Sperm density fell rapidly, but the method was ineffective in 3.6% of men. The dosing regimen with testosterone administration every 6 months did not maintain the contraceptive effect all along the treatment while the administration every 4 months did. A total of 11% of men discontinued the treatment for problems with pellets (dislike implants; extrusion; pain) and 5.5% for medical reasons (androgen deficiency, mood fluctuation). (Turner L. et al., J. CLIN. ENDOCRINOL. METAB., (2003) 88(10) 4659-4667.

Homonnai Z T et al. describe that phenoxybenzamine (PBZ), administered in doses up to 20 mg/day, causes aspermia following male orgasm. In 2 to 3 days, PBZ blocks ejaculation and this is fully reversed with the cessation of treatment. Homonnai Z T et al., CONTRACEPTION, (1984).29(5) 479-491. PBZ is currently approved to control episodes of hypertension and sweating associated with pheochromocytoma. Its ability to decrease blood pressure may be an issue to develop PBZ as a contraceptive.

WO 2008/087421 discloses compounds of the following formula:

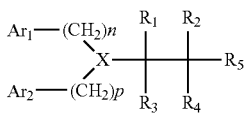

wherein Ar1, Ar2, R1, R2, R3, R4, R5, n and p are as defined in WO 2008/087421, useful for male contraception by reduction or prevention of the emission of sperm. After administration of one of these compounds, the volume of sperm emitted during orgasm is reduced by at least 50% which is insufficient to constitute a contraceptive effect.

It is clear that development of a male contraceptive is a major medical challenge and there is still a need for an effective reversible male contraceptive.

This invention aims at providing compositions and methods for male contraception using a non-hormonal molecule, thereby avoiding the side effects linked to the use of hormones, especially sexual, behavioral, physiological, and psychological side effects associated with hormonal treatments. The contraceptive method of the invention may be enteral, particularly oral, buccal or sublingual, and can be self-administered. The contraception method of this invention presents a lengthened contraceptive effect, particularly after the first two administrations of the composition. Oral, buccal, sublingual or transdermal administration may be discretely carried out without need for any external device. The compositions and methods of the invention further ensure convenience and reversibility.

Alpha-1-adrenoreceptor (or "adrenoceptor") antagonists (also known as alpha-1 blockers or alpha-adrenergic blocking agents) make up a class of drugs that block $\alpha_1$-adrenergic receptors in arteries, smooth muscles, and central nervous system tissues. When administered in humans, they prevent the hormone norepinephrine from tightening the muscles in the walls of smaller arteries and veins, which causes the vessels to remain open and relaxed. This improves blood flow and lowers blood pressure. Because alpha blockers also relax other muscles throughout the body, these medications can help improve urine flow in older men with prostate problems such as Benign Prostatic Hyperplasia ("BPH").

For example, the alpha-1-adrenoreceptor antagonist tamsulosin is sold commercially as tamsulosin hydrochloride ((−)-(R)-5-[2-[[2-(o-Ethoxyphenoxy) ethyl]amino]propyl]-2-methoxybenzenesulfonamide, monohydrochloride) under the trade name, e.g., Flomax® for the treatment of BPH. Wang et al. reported a dose dependent decrease in the volume of semen after a single dose of 0.4 or 0.8 mg of tamsulosin (Wang J et al., *Assessment of Tamsulosin as a Potential Male Contraceptive in Healthy Volunteers*. UROLOGY (2012) 80: 614-617). The volume of semen was evaluated 4 to 6 hours after dosing. An ejaculation was reached with the 0.8-mg dose, and the authors reported that "functional sperm count was significantly reduced. Side effects including discomfort on ejaculation were reported by some subjects.

Silodosin, also known as (−)-(R)-1-(3-hydroxypropyl)-5-[2-[[2-[2-(2,2,2-trifluoroethoxy)phenoxy]ethyl]amino]propyl]indoline-7-carboxamide, is a highly selective alpha-1a-adrenoreceptor antagonist that is also currently known and used in the treatment of BPH. Currently, it is marketed and sold as a BPH treatment under the brand name Rapaflo®. In vitro studies in humans have proved the uroselectivity of silodosin, which affects the contraction of the prostatic smooth muscle (Moriyama N, Akiyama K, Murata S, et al., *KMD-3213, a novel alpha1A-adrenoceptor antagonist, potently inhibits the functional alpha1-adrenoceptor in human prostate*. EUR J PHARMACOL. 1997; 331(1):39-42) (Akiyama K, Tatemichi S, Katayama S, et al. *Relationship between prostatic alpha(1)-adrenoceptor binding and reduction in intraurethral pressure following continuous infusion of KMD-3213 in rats*. PHARMACOLOGY. 2002; 64(3): 140-147), to be greater than that of other alpha-1 blockers, such as tamsulosin and naftopidil (Tatemichi S, Tomiyama Y, Maruyama I, et al. *Uroselectivity in male dogs of silodosin (KMD-3213), a novel drug for the obstructive component of benign prostatic hyperplasia*. NEUROUROL URODYN. 2006; 25(7):792-799. discussion 800-801).

One side effect of silodosin, when administered in amounts to treat BPH, is retrograde ejaculation (RE), also known as a decrease or absence of semen during ejaculation. For example, Sakata K. et al. demonstrated that the administration of silodosin at 4 mg twice a day induced ejaculatory disorder at a high incidence (K. Sakata et al., BMC Urology 2012, 12:29). Kobayashi et al. reported that 4 mg silodosin given twice a day for 3 days, induced a complete lack of seminal emission on healthy volunteers (Kobayashi et al., International Journal of Impotence Research 2009, 21, 306-310). Kobayashi et al. also show a 100% rate of discomfort upon ejaculation for male subjects treated with silodosin (Kobayashi K, et al. *Inhibition of seminal emission is the main cause of anejaculation induced by a new highly selective α1A-blocker in normal volunteers.* J. SEX MED (2008) 5:2185-2190), while Shimizu et al. report a decrease in quality of orgasm (Shimizu F, et al. *Impact of dry ejaculation caused by highly selective alpha1A-blocker: randomized, double-blind, placebo-controlled crossover pilot study in healthy volunteer men.* J. SEX MED. (2010) 7(3):1277-83). Other studies show a decrease in erectile function (Bozkurt O, et al. *Silodosin causes impaired ejaculation and enlargement of seminal vesicles in sexually active men treated for lower urinary tract symptoms suggestive of benign prostatic hyperplasia.* UROLOGY (2015) 85(5):1085-9) and sexual desire (Capogrosso P, et al. *Effects of silodosin on sexual function—realistic picture from the everyday clinical practice.* ANDROLOGY (2015) 3:1076-1081).

Additionally, the effect of the alpha-1a blockers on the ejaculatory function is known to be dose-dependent (see e.g., Hisasue S I, et al. *Ejaculatory disorder caused by alpha-1 adrenoceptor antagonists is not retrograde ejaculation but a loss of seminal emission.* INTERNATIONAL JOURNAL OF UROLOGY (2006) 13:1311-1316).

In the prior art, Bhat et al (INDIAN JOURNAL OF UROLOGY (2018) 34(5): S7) reported a study aiming at evaluating the efficacy of silodosine 8 mg as on-demand, reversible, male oral contraceptive. The study was carried out in several parts. In a first part, participants received silodosine 8 mg for 7 days and were evaluated 2 hours after intake (the results were: no spermatozoa in the semen and post-analysis urine). In a second part, Day 8 to 15, they received placebo (the result was: no information in the first two days, normal semen analysis from day 2 of placebo). In a third part, during 6 months, they had on demand silodosine 8 mg, sporadically, prior to the sexual intercourse. At that time, they were not evaluated and the study states that no unintended pregnancy was reported. Bhat et al reports an on-demand male contraception. However, Bhat et al does not fulfill the needs of the subjects who ask for a safe contraceptive method ensuring a continuous contraceptive effect, where they are confident that they are not exposed to a fertility risk.

Presently, however, no treatment profile has been developed that would allow for daily contraceptive use, as well as a regular (preferably 24 hour) duration of action allowing a daily, continuous use. Ideally, for the purposes of establishing familiarity and compliance in male subjects, such a treatment profile would resemble female hormonal contraceptive pills, for example, that the pills are to be administered at the same time every day. Such a treatment profile would also include some of the benefits associated with female hormonal contraceptive pills, namely, that a subject's failure to take one pill for as long as twenty-four hour period does not impact the contraceptive effect. Still further, there would also be beneficial differences between female hormonal contraceptives and the non-hormonal male contraceptives described herein. For example, women's hormonal contraceptives are typically provided in 28-day supply, including three weeks of "active" pills that contain the hormone or hormones necessary to prevent pregnancy, and one week of placebo pills, administered to allow the female subject to experience menstruation-like withdrawal bleeding.

Accordingly, it would be desirable for a non-hormonal composition and method for providing male contraception, which would allow for the features and benefits as described herein. Such compositions and methods would not impact the erectile function, sexual desire, ejaculation, and quality of orgasm, of the male subject nor induce undesirable side effects that would discourage male subjects from using it. Also such compositions and methods would show sufficient contraception efficacy so that the female partner will not want to use backup contraception of her own.

SUMMARY OF THE INVENTION

This invention aims at providing a male contraceptive method, where side effects are highly limited, administration is simple, effect is reversible, and as in female contraception, when a delay occurs, compared to the recommended administration scheme, such delay does not impair the effectiveness. For the purposes of establishing familiarity and compliance in male subjects, such a treatment method shall resemble to female hormonal contraceptive methods where a once-a-day pill is to be administered at the same time every day and a subject's delay in taking one pill for as long as twenty-four-hours does not impact the contraceptive effect.

Even though some pieces of prior art reported a pharmacological effect, i.e. an aspermia when alpha-adrenergic antagonists were administered, to the knowledge of the Applicant, none of the prior art documents ever described or suggested that alpha-1 adrenoceptor antagonists, especially alpha-1a adrenoceptor antagonists, could meet all the requirements and criteria of a continuous male contraceptive method that would be suitable for a large population without much restrictions, altogether.

Up to the present invention, no administration profiles for male contraception comprising a once daily administration and with a regular duration of action were ever proposed. Surprisingly, the Applicant found out that a male contraceptive method could be envisaged, and that a daily alpha-1 adrenoceptor antagonist administration could, under certain conditions, fulfill all the criteria set forth hereabove. The use of the compositions according to the invention further ensures convenience and reversibility.

Furthermore, to the Applicants surprise, it was found that the pharmacokinetic profile of this male contraception method may not be influenced in a clinically meaningful manner by concomitant food consumption, which is a significant improvement in terms of benefit vs. risk assessment of the invention and subject compliance to the treatment.

Also surprisingly, the Applicant shows that, in a subject implementing the method of the invention, the quality of orgasm and the erectile function are preserved, as shown by the unchanged numerical rating scale (NRS) score for subjective quality of orgasms and unchanged international index of erectile function (IIEF): a multidimensional scale for assessment of erectile dysfunction.

This invention relates to the use of a composition in a non-hormonal contraception method for a male subject, wherein said composition is an extended release formulation comprising:
 an alpha-1-adrenoreceptor antagonist; and
 at least one pharmaceutically acceptable carrier,
wherein the contraception method includes a once daily administration of said composition at about the same time each day, triggering a continuous reversible aspermia, azoospermia, or severe oligozoospermia in the male subject, and wherein after an initial period of at least two consecutive days, the contraception is not impaired by a delay of the subsequent once daily intake.

According to one embodiment, the composition is administered orally. According to another embodiment, after the initial period of consecutive days, the intake of a next dose administration can be delayed from 6 to 18 hours after the last regular daily dose time, and the condition of aspermia, azoospermia or severe oligozoospermia is maintained in the male subject.

According to another embodiment, after the initial period of consecutive days, failure to intake one daily dose does not affect the continuous state of aspermia, azoospermia or severe oligozoospermia supporting the contraception method for 36 to 48 hours as of the last intake time.

According to another embodiment, the contraception method is carried on for at least eight days. According to another embodiment, the alpha-1-adrenoreceptor antagonist is in an amount ranging from about 0.1 to about 30 mg, preferably from about 0.2 to about 20 mg. According to another embodiment, the alpha-1-adrenoreceptor antagonist is (R)-silodosin. According to another embodiment, (R)-silodosin is in a polymorphic or amorphous form. According to another embodiment, the composition is formulated in an extended release formulation. According to another embodiment, the composition includes or consists of at least one particle, preferably at least one coated particle, and the average particle diameter is in the range of 0.01 to 5 mm, preferably 0.1 to 2 mm. According to another embodiment, the particles are encompassed into a capsule, each capsule being filled by particles in a number sufficient to reach the daily dose. According to another embodiment, the contraception is achieved independently from the food consumption by the male subject. According to another embodiment, the daily administration contraception method further comprises a simultaneous or sequential administration of an additional composition suitable for treating erectile dysfunction; preferably the additional composition comprises a phosphodiesterase-5 inhibitor.

This invention also relates to a packaging comprising at least 7, 14, 28, 56, 84, or 168 to 365 unitary doses; or 10, 20, 30, 60, 90, or 180 to 360 unitary doses of the composition of the invention, each unitary dose being a daily dose. According to one embodiment, the composition includes an alpha-1-adrenoreceptor antagonist in an amount ranging from about 0.1 to about 30 mg, preferably from about 0.2 to about 20 mg, preferably the alpha-1-adrenoreceptor antagonist is (R)-silodosin in an amount of 8 to 12 mg.

The present invention comprises a composition for daily administration to a male subject, the composition comprising an alpha-1-adrenoreceptor antagonist; and a pharmaceutically acceptable carrier, wherein the composition induces a condition of aspermia, azoospermia, or severe oligozoospermia in the male subject.

In one embodiment, the present invention comprises a composition for administration to a male subject, the composition comprising a pharmaceutically effective amount of (R)-silodosin for inducing and maintaining aspermia, azoospermia, or severe oligozoospermia in the male subject; and a pharmaceutically acceptable carrier, wherein the composition is in microgranule form, the microgranules being formulated in a capsule, and wherein the (R)-silodosin has the following structure:

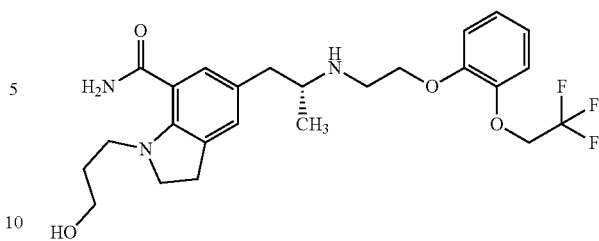

In a separate aspect, the present invention comprises a composition for daily administration to a male subject, the composition comprising a pharmaceutically effective amount of (R)-silodosin; and a pharmaceutically acceptable carrier, wherein the (R)-silodosin has the following structure:

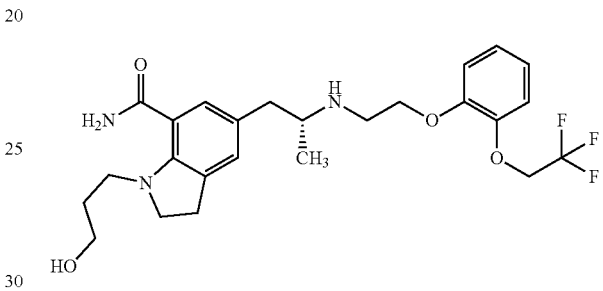

and wherein the composition induces a state of aspermia, azoospermia, or severe oligozoospermia in the male subject.

In a separate aspect, the present invention comprises a method for inducing a contraceptive effect in a male subject. The method comprises administering a composition comprising an alpha-1-adrenoreceptor antagonist and a pharmaceutically acceptable carrier to the patient.

In a separate aspect, the present invention comprises a method for inducing aspermia, azoospermia, and/or severe oligozoospermia in a male subject. The method comprises administering a composition comprising an alpha-1-adrenoreceptor antagonist and a pharmaceutically acceptable carrier to the patient. In the claimed method, the composition is administered daily to the patient.

In a further embodiment, the present invention comprises a method for inducing a continuous state of aspermia, azoospermia, or severe oligozoospermia in a male subject. The method comprises administering on a daily dosing regimen an oral composition comprising an alpha-1-adrenoreceptor antagonist and a pharmaceutically acceptable carrier to the patient at the same time each day. In the claimed method, failure to administer one daily dose during the daily dosing regimen to the male subject does not affect the continuous state of aspermia, azoospermia, or severe oligozoospermia.

In one embodiment, the present invention comprises a composition for inducing a condition of aspermia, azoospermia, or severe oligozoospermia in the male subject in order to prevent pregnancy in a female partner, the composition comprising daily administration of a pharmaceutically effective amount of (R)-silodosin, wherein the (R)-silodosin has the following structure:

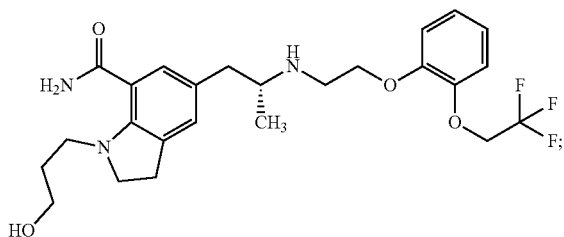 [SMILES: C[C@H](Cc1cc2c(c(C(N)=O)c1)N(CCCO)CC2)NCCOc1ccccc1OCC(F)(F)F]

and a pharmaceutically acceptable carrier, wherein the composition may be administered with or without food.

In a separate aspect, the present invention comprises a method for inducing a contraceptive effect in a male subject. The method comprises administering a composition comprising an alpha-1-adrenoreceptor antagonist and a pharmaceutically acceptable carrier to the patient. Administration of the composition occurs at the same time, or about the same time, within a twenty-four hour dosing period, In a separate aspect, the present invention comprises a pharmaceutical composition comprising: a single daily oral dosage form comprising about 12 mg of (R)-silodosin, wherein the (R)-silodosin has the following structure:

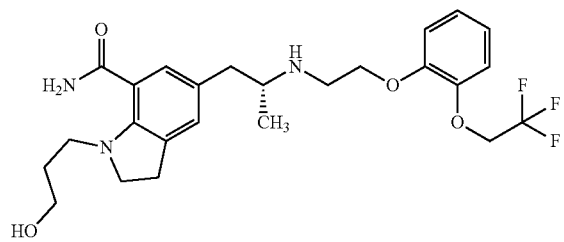

wherein, upon achievement of a steady state in administration to a male subject, said pharmaceutical composition provides a pharmacokinetic profile of said silodosin having i) a median $T_{max}$ ranging from about 3 hours to about 8 hours; and ii) a mean $C_{max}$ which is less than about 70 ng/mL.

In another aspect, described herein is a method of inducing a reversible condition of aspermia, azoospermia or severe oligozoospermia in a male subject sufficient for contraceptive effect, the method comprising administering once daily doses of a composition comprising: an extended release formulation of alpha-1-adrenoreceptor antagonist in an amount effective, when administered on a once daily dosing regimen, to induce a reversible condition of aspermia, azoospermia or severe oligozoospermia sufficient for contraceptive effect in the male subject; and a pharmaceutically acceptable carrier, wherein the failure to administer one daily dose after an initial period of two consecutive days does not affect the continuous state of aspermia, azoospermia or severe oligozoospermia sufficient for contraceptive effect in the male subject.

In one embodiment, the initial period of consecutive days is at least two consecutive days, with administration at about the same time each day. In another embodiment, the initial period of consecutive days is at least 5 days.

In another embodiment, the method is suitable for short term, at least 8 days, to long term treatment.

In another embodiment, successive daily doses may be missed or omitted such that no dose is administered for more than about 48 hours. For example, in one embodiment, after an initial period of successive days' regular dosing, two successive daily doses can be missed or omitted without affecting contraceptive effect in the male subject. That is, after an initial period of successive days' regular dosing, failure to administer doses for about 48 hours does not affect the continuous state of aspermia, azoospermia or severe oligozoospermia sufficient for contraceptive effect in the male subject.

In another embodiment, the amount of alpha-1-adrenoreceptor antagonist in the composition administered once daily is about 4 to about 12 mg.

In another embodiment, the alpha-1-adrenoreceptor antagonist is (R)-silodosin. In one embodiment, the amount of (R)-silodosin in the composition administered once daily is about 4 to about 12 mg. In another embodiment, the amount of (R)-silodosin in the composition administered once daily is about 8 mg.

In another embodiment, the composition is administered orally.

In another embodiment, the composition is simultaneously or sequentially co-administered with a composition suitable for treating erectile dysfunction; as a non-limiting example, the additional composition can be a phosphodiesterase-5 (PDE5) inhibitor.

In another embodiment, the male subject suffers from benign prostatic hyperplasia (BPH). In another embodiment, the male subject suffers from BPH and erectile dysfunction.

In another embodiment, the composition can be administered with or without food, without interrupting or affecting the continuous contraceptive effect.

In another embodiment, the extended release formulation comprises a microgranule form. In one embodiment, the microgranules are less than 2 millimeters in diameter. In another embodiment, the microgranules have a density greater than or equal to about 1.

In another aspect, described herein is a method for reversible, continuous, non-hormonal contraception in a male subject, the method comprising administering once daily doses of a composition comprising: an extended release formulation of alpha-1-adrenoreceptor antagonist in an amount effective, when administered on a once daily dosing regimen, to induce a reversible condition of aspermia, azoospermia or severe oligozoospermia sufficient for contraceptive effect in the male subject; and a pharmaceutically acceptable carrier, wherein the failure to administer one daily dose after an initial period of two consecutive days does not affect the continuous state of aspermia, azoospermia or severe oligozoospermia sufficient for contraceptive effect in the male subject.

In another aspect, described herein is a method for birth control, the method comprising administering to a male subject once daily doses of a composition comprising: an extended release formulation of alpha-1-adrenoreceptor antagonist in an amount effective, when administered on a once daily dosing regimen, to induce a reversible condition of aspermia, azoospermia or severe oligozoospermia sufficient for contraceptive effect in the male subject; and a pharmaceutically acceptable carrier, wherein the failure to administer one daily dose after an initial period of two consecutive days does not affect the continuous state of aspermia, azoospermia or severe oligozoospermia sufficient for contraceptive effect in the male subject.

In another aspect, described herein is a composition for daily administration to a male subject, the composition comprising: an alpha-1-adrenoreceptor antagonist; and a pharmaceutically acceptable carrier, wherein the composition induces a condition of aspermia, azoospermia, or severe oligozoospermia in the male subject.

In one embodiment, alpha-1-adrenoreceptor antagonist is (R)-silodosin and has the following structure:

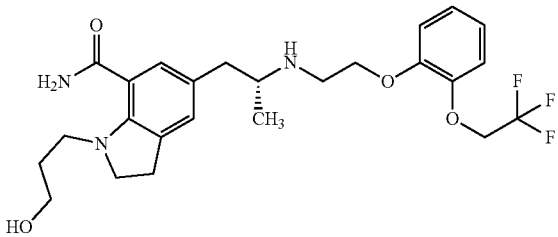 [SMILES: C[C@H](Cc1cc2c(c(C(N)=O)c1)N(CCCO)CC2)NCCOc1ccccc1OCC(F)(F)F]

In another embodiment, the composition comprises a polymorphic form of (R)-silodosin.

In another embodiment, the sperm count of the male subject after administration of the composition is less than or equal to about $1 \times 10^6$ sperm per ejaculate.

In another embodiment, the (R)-silodosin is administered in the amount of about 4 mg, about 6 mg, about 8 mg, or about 12 mg. In another embodiment, the (R)-silodosin is administered in the amount of between about 4 and about 20 mg. In another embodiment, the (R)-silodosin is administered in the amount of between about 2 and about 30 mg.

In another embodiment, the composition is formulated into one or more of the following dosage forms selected from the group consisting of subdermal implant, transdermal patch and injectable.

In another embodiment, the composition is formulated in one or more oral dosage forms being any one or a combination selected from the group consisting of: soft-gels, caplets, pills, tablets, capsules, hydromatrix tablets, and osmotic tablets.

In another embodiment, the composition is in microgranule form. In another embodiment, the microgranules are formulated in a capsule, the capsule further optionally comprising a controlled release coating. In another embodiment, the microgranules are less than about 2 millimeters in diameter. In another embodiment, the microgranules have a density greater than or equal to about 1.

In another embodiment, the composition is in microtablet form.

In another embodiment, the microtablets are formulated in a capsule, the capsule further optionally comprising a controlled release coating. In another embodiment, the microtablets are less than about 2 millimeters in diameter. In another embodiment, the microtablets are less than about 2 millimeters in length. In another embodiment, the microtablets have a density of greater than or equal to about 1.

In another embodiment, the composition is formulated into a coated tablet comprising a matrix tablet of (R)-silodosin surrounded by a controlled release coating.

In another embodiment, the composition is formulated into a hydromatrix tablet comprising (R)-silodosin and a hydrophilic excipient.

In another embodiment, the tablet is a mono-layer tablet. In another embodiment, the tablet is a multi-layer tablet.

In another embodiment, the composition is suitable for contraceptive use. In another embodiment, the composition is administered to the male subject at about the same time each day.

In another embodiment, the composition maintains the condition of aspermia, azoospermia, or severe oligozoospermia in the male subject for at least about one hour, at least about three hours, at least about six hours, at least about twelve hours, at least about twenty-four hours, at least about 36 hours, at least about 48 hours or more.

In another embodiment, the composition does not impair erectile function of the male subject. In another embodiment, the composition does not impair the quality of orgasm of the male subject. In another embodiment, the composition does not cause discomfort upon ejaculation for the male subject.

In another embodiment, the composition is optionally administered with food.

In another aspect, described herein is a composition for administration to a male subject, the composition comprising: a pharmaceutically effective amount of (R)-silodosin for inducing and maintaining aspermia, azoospermia, or severe oligozoospermia in the male subject; and a pharmaceutically acceptable carrier, wherein the composition is in microgranule form, the microgranules being formulated in a capsule, and wherein the (R)-silodosin has the following structure:

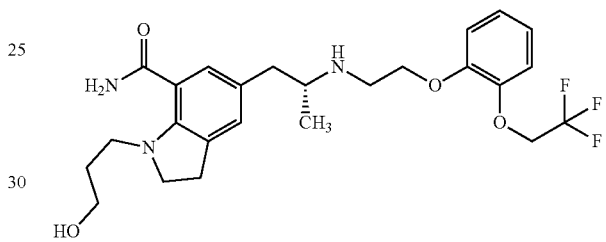

In one embodiment, the microgranules comprise: an inert core; a drug layer of (R)-silodosin applied to the inert core, and a controlled release coating surrounding the drug layer. In another embodiment, the composition further comprises an optional seal coat layer.

In another embodiment, the drug layer comprises (R)-silodosin and a binder.

In another embodiment, the drug layer further comprises one or more of the following: a surfactant, a stabilizing agent, a lubricant, and a disintegrant.

In another embodiment, the microgranules are matrix microgranules of (R)-silodosin surrounded by a controlled release coating.

In another aspect, described herein is a composition for administration to a male subject, the composition comprising: a pharmaceutically effective amount of (R)-silodosin; and a pharmaceutically acceptable carrier, wherein the (R)-silodosin has the following structure:

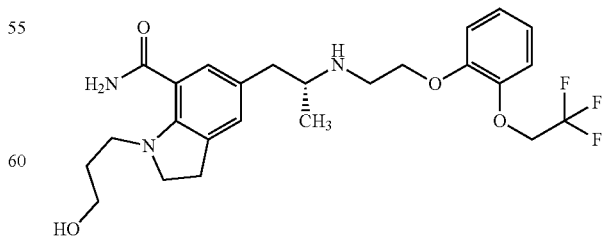

In one embodiment, the composition induces the state of aspermia, azoospermia, or severe oligozoospermia immediately upon administration of an initial dose.

In another embodiment, the composition of any of the preceding aspects is formulated in one or more of the following dosage forms: orally disintegrating tablets, orally disintegrating pellets, orally disintegrating granules, oral film, nasal spray, sublingual tablets, buccal tablets, adhesive tablets, adhesive films, and transmucosally delivered solutions.

In another aspect, described herein is a method for inducing a contraceptive effect in a male subject, the method comprising: administering a composition comprising an alpha-1-adrenoreceptor antagonist and a pharmaceutically acceptable carrier to the patient.

In one embodiment, the method further comprises daily administration of the alpha-1-adrenoreceptor antagonist (R)-silodosin having the following structure:

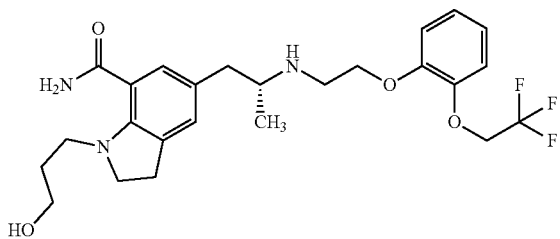 [SMILES: C[C@H](Cc1cc2c(c(C(N)=O)c1)N(CCCO)CC2)NCCOc1ccccc1OCC(F)(F)F]

In another embodiment, a contraceptive effect is achieved by administration of at least two consecutive daily doses of the alpha-1-adrenoreceptor. In another embodiment, the daily administration of the alpha-1-adrenoreceptor is performed at about the same time on each day over a four week period. In another embodiment, the daily administration of the alpha-1-adrenoreceptor can be delayed on the second day of two consecutive days, such that the administration of the second dose occurs more than about twenty-four hours after administration of a first dose. In another embodiment, the daily administration of a second dose of two consecutive doses of the alpha-1-adrenoreceptor can be delayed, such that the administration of the second dose occurs about twenty-five hours after administration of a first dose. In another embodiment, the daily administration of a second dose of two consecutive doses of the alpha-1-adrenoreceptor can be delayed, such that the administration of the second dose occurs about twenty-seven hours after administration of a first dose. In another embodiment, the daily administration of a second dose of two consecutive doses of the alpha-1-adrenoreceptor can be delayed, such that the administration of the second dose occurs more than about thirty-six hours after administration of a first dose. In another embodiment, the daily administration of a second dose of two consecutive doses of the alpha-1-adrenoreceptor can be delayed, such that the administration of the second dose occurs about forty-two hours after administration of a first dose. In another embodiment, the daily administration of a second dose of two consecutive doses of the alpha-1-adrenoreceptor can be delayed, such that the administration of the second dose occurs about forty-eight hours after administration of a first dose. In another embodiment, the daily administration of a second dose of two consecutive doses of the alpha-1-adrenoreceptor can be delayed, such that the administration of the second dose occurs about seventy-two hours after administration of a first dose. In another embodiment, the daily administration of a second dose of two consecutive doses of the alpha-1-adrenoreceptor can be delayed, such that the administration of the second dose occurs about ninety-six hours after administration of a first dose. In another embodiment, the contraceptive effect is not inhibited by such delay of the second dose.

In another embodiment, the subject can use a back-up birth control method.

In another embodiment, the alpha-1-adrenoreceptor is administered with food. In another embodiment, the alpha-1-adrenoreceptor is administered without food.

In another embodiment, the (R)-silodosin is administered in the amount of about 12 mg. In another embodiment, the (R)-silodosin is administered in the amount of between about 8 and about 12 mg. In another embodiment, the (R)-silodosin is administered in the amount of between about 16 and about 20 mg.

In another embodiment, the composition is formulated in one or more oral dosage forms being any one or a combination selected from the group consisting of: soft-gels, caplets, pills, tablets, capsules, hydromatrix tablets, and osmotic tablets.

In another embodiment, the delay of a single daily dose in the daily administration of the (R)-silodosin does not impact the contraceptive effect on the male subject. In another embodiment, the delay of the single daily dose in the daily administration of the (R)-silodosin is about one hour. In another embodiment, the delay of the single daily dose in the daily administration of the (R)-silodosin is about two hours. In another embodiment, the delay of the single daily dose in the daily administration of the (R)-silodosin is about three hours. In another embodiment, the delay of the single daily dose in the daily administration of the (R)-silodosin is about six hours. In another embodiment, the delay of the single daily dose in the daily administration of the (R)-silodosin is about twelve hours. In another embodiment, the delay of the single daily dose in the daily administration of the (R)-silodosin is about twenty-four hours. In another embodiment, such delay does not impact the contraceptive effect on the male subject.

In another embodiment, the omission of a single daily dose in the daily administration of the (R)-silodosin does not impact the contraceptive effect on the male subject.

In another embodiment, the composition does not impair erectile function of the male subject. In another embodiment, the composition does not impair the quality of orgasm of the male subject. In another embodiment, the composition does not cause discomfort upon ejaculation for the male subject.

In another aspect, described herein is a method for inducing aspermia, azoospermia, and/or severe oligozoospermia in a male subject, the method comprising: administering a composition comprising an alpha-1-adrenoreceptor antagonist and a pharmaceutically acceptable carrier to the patient, wherein the composition is administered daily. In one embodiment, the alpha-1-adrenoreceptor antagonist is (R)-silodosin and has the following structure:

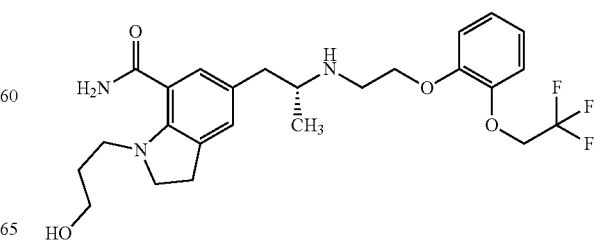

In one embodiment, the composition is co-administered with a second pharmaceutical composition. In one embodiment, the composition is co-administered with a phosphodiesterase-5 (PDE5) inhibitor. In another embodiment, the second pharmaceutical composition is suitable for treating erectile dysfunction. In another embodiment, the composition and the PDE5 inhibitor are administered to the male patient at different times. In another embodiment, the composition and the PDE5 inhibitor are administered to the male patient at the same time. In another embodiment, the compositions are not administered with food. In another embodiment, the compositions are administered with food.

In another embodiment, the male subject suffers from erectile dysfunction.

In another embodiment, the male subject suffers from Benign Prostatic Hyperplasia (BPH). In another embodiment, the male subject suffers from both erectile dysfunction and BPH.

In another embodiment, the composition does not impair erectile function of the male subject. In another embodiment, the composition does not impair the quality of orgasm of the male subject. In another embodiment, the composition does not cause discomfort upon ejaculation for the male subject.

In another aspect, described herein is a method for inducing a continuous state of aspermia, azoospermia, or severe oligozoospermia in a male subject, the method comprising: administering on a daily dosing regimen an oral composition comprising an alpha-1-adrenoreceptor antagonist and a pharmaceutically acceptable carrier to the patient at the same time each day, wherein failure to administer one daily dose during the daily dosing regimen to the male subject does not affect the continuous state of aspermia, azoospermia, or severe oligozoospermia.

In one embodiment, the alpha-1-adrenoreceptor antagonist is (R)-silodosin and has the following structure:

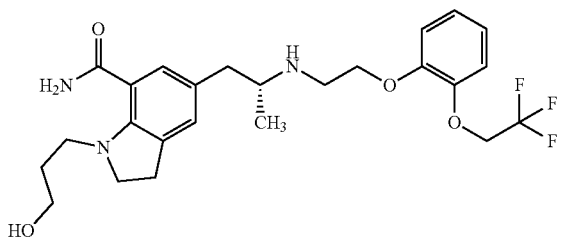 [SMILES: C[C@H](Cc1cc2c(c(C(N)=O)c1)N(CCCO)CC2)NCCOc1ccccc1OCC(F)(F)F]

In another embodiment, the failure to administer two continuous daily doses within one week of the daily dosing regimen does not affect the continuous state of aspermia, azoospermia, or severe oligozoospermia. In another embodiment, the failure to administer three continuous daily doses within one week of the daily dosing regimen does not affect the continuous state of aspermia, azoospermia, or severe oligozoospermia. In another embodiment, the failure to administer two non-continuous daily doses within one week of the daily dosing regimen does not affect the continuous state of aspermia, azoospermia, or severe oligozoospermia. In another embodiment, the failure to administer three non-continuous daily doses within one week of the daily dosing regimen does not affect the continuous state of aspermia, azoospermia, or severe oligozoospermia.

In another embodiment, the daily dosing regimen occurs at about the same time each day.

In another embodiment, the administration of the daily dosing regimen does not occur at about the same time each day, but each daily dose is administered within twenty-four hours of the previous daily dose.

In another aspect, described herein is a composition for inducing a condition of aspermia, azoospermia, or severe oligozoospermia in the male subject in order to prevent pregnancy in a female partner, the composition comprising daily administration of: a pharmaceutically effective amount of (R)-silodosin, wherein the (R)-silodosin has the following structure:

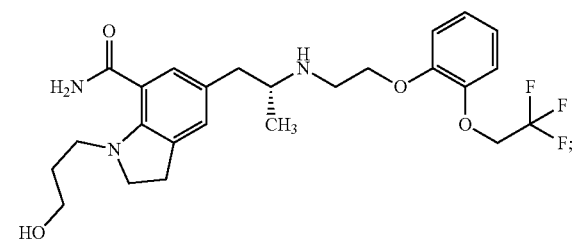 [SMILES: C[C@H](Cc1cc2c(c(C(N)=O)c1)N(CCCO)CC2)NCCOc1ccccc1OCC(F)(F)F]

and a pharmaceutically acceptable carrier, wherein the composition can be administered with or without food.

In another aspect, described herein is a method for inducing a contraceptive effect in a male subject, the method comprising: administering, at the same time or about the same time within a twenty-four hour dosing period, a composition comprising an alpha-1-adrenoreceptor antagonist and a pharmaceutically acceptable carrier to the patient.

In one embodiment, the alpha-1-adrenoreceptor antagonist is (R)-silodosin, having the structure described herein.

In one embodiment, the twenty-four hour dosing period can be extended by about 30 minutes, about one hour, about two hours, about three hours, about six hours, about twelve hours, about twenty-four hours, about thirty-six hours, about forty-eight hours or by about seventy-two hours without altering the contraceptive effect of the alpha-1-adrenoreceptor antagonist.

In another aspect, described herein is a pharmaceutical composition comprising: a single daily oral dosage form comprising about 12 mg of (R)-silodosin, wherein the (R)-silodosin has the following structure:

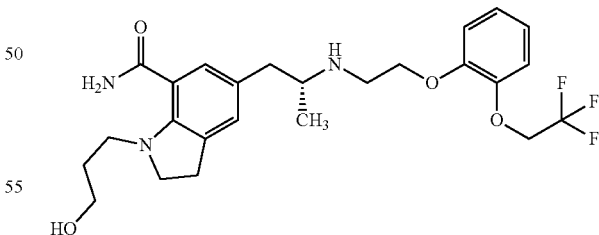

wherein, upon achievement of a steady state in administration to a male subject, the pharmaceutical composition provides a pharmacokinetic profile of the silodosin having i) a $T_{max}$ ranging from about 3 hours to about 10 hours; and ii) a mean $C_{max}$ which is less than about 70 ng/mL.

In another aspect, described herein is a pharmaceutical composition comprising: a single daily oral dosage form comprising about 8 mg of (R)-silodosin, wherein the (R)-silodosin has the following structure:

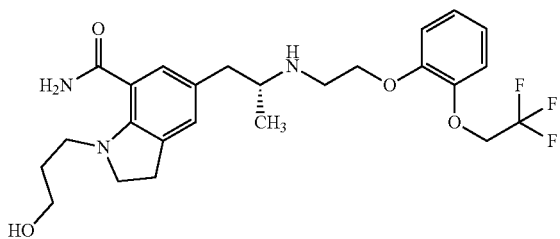 [SMILES: C[C@H](Cc1cc2c(c(C(N)=O)c1)N(CCCO)CC2)NCCOc1ccccc1OCC(F)(F)F]

and wherein, upon achievement of a steady state in administration to a male subject, the pharmaceutical composition provides a pharmacokinetic profile of said silodosin having i) a $T_{max}$ ranging from about 3 hours to about 10 hours; and ii) a mean $C_{max}$ which is less than about 50 ng/mL.

In a separate aspect, the present invention comprises a pharmaceutical composition comprising: a single daily oral dosage form comprising about 8 mg of (R)-silodosin, wherein the (R)-silodosin and has the following structure:

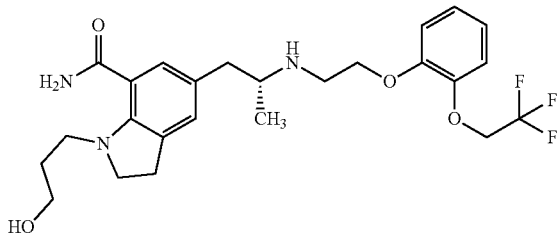

wherein, upon achievement of a steady state in administration to a male subject, said pharmaceutical composition provides a pharmacokinetic profile of said silodosin having i) a median $T_{max}$ ranging from about 3 hours to about 8 hours; and ii) a mean $C_{max}$ which is less than about 50 ng/mL.

DETAILED DESCRIPTION OF THE EXEMPLARY EMBODIMENTS

Figure 1:
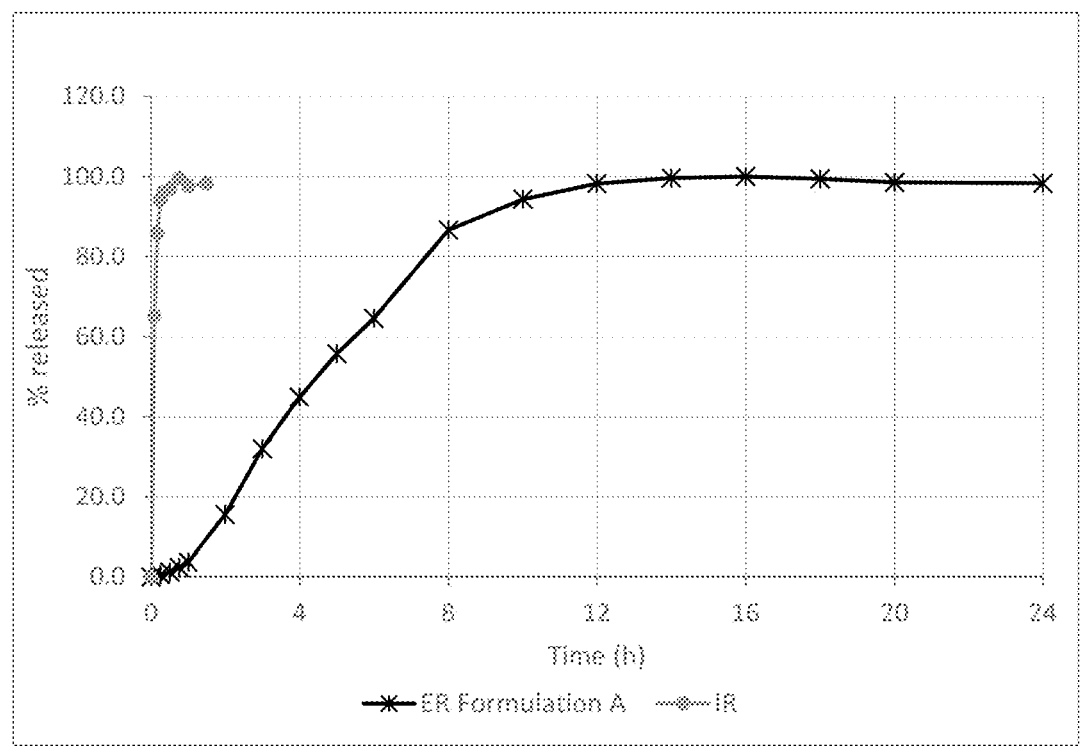
FIG. 1 is a graph illustrating the dissolution rate of the extended release (ER) formulation A of (R)-Silodosin, in comparison with the dissolution rate of an immediate release (IR) formulation of (R)-Silodosin

It is understood that the present invention is not limited to the particular methodologies, protocols, fillers, and excipients, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention. All references cited herein are incorporated by reference herein in their entirety.

The term "About", as used herein, means approximately, roughly, around, or in the region of. When the term "about" is preceding a figure means plus or less 20% of the value of said figure. When the term "about" is used in conjunction with a numerical range, it modifies that range by extending the boundaries above and below the numerical values set forth by 20%.

The term "subject," as used herein, comprises any and all organisms and includes the term "patient." "Subject" may refer to a human or any other animal. Subjects may be referred to as "male subject(s)" or "female subject(s)" depending on their respective sex. In one embodiment, the "subject" is a healthy male human subject. In a second embodiment, the subject is a male human suffering from erectile dysfunction. In a third embodiment, the subject is a male human suffering from benign prostatic hyperplasia (BPH). In a fourth embodiment, the subject is a male human suffering from both benign prostatic hyperplasia (BPH) and erectile dysfunction.

The phrase "co-administration" refers to administration of two or more compositions to a subject together, which includes administration at about the same time or within a certain specific or desired time.

The term "Contraceptive method" as used herein, means a method which is defined by an administration scheme and a rule of oblivion (possibility to accept a delay in the uptake, without down effect), which sustain the contraceptive effect of the drug and make it efficient and suitable for regular and wide use by a general population. In other words, in a contraceptive method in the meaning of this invention, failure to administer one daily dose during the daily dosing regimen to the male subject may not affect the continuous state of aspermia, azoospermia, or severe oligozoospermia especially if the failure occurs after a continuous administration of at least 2, preferably at least 5 preceding days.

The phrase "dissolvable form" refers to any compositions that dissolve into a solution in the mouth, such as, for example, buccally or sublingually. Such compositions, in one embodiment, may dissolve within about 60 seconds or less after placement in the mouth without any chewing.

The phrase "pharmaceutically acceptable," as used herein, refers to those compounds, materials, compositions and/or dosage forms which are, within the scope of sound pharmaceutical/medical judgment, suitable for use in contact with the tissues of human beings and animals without excessive toxicity, irritation, allergic response, or other problem or complication, commensurate with a reasonable benefit/risk ratio. Thus, the phrase "pharmaceutically acceptable carriers," as used herein, refers to such suitable compounds and materials defined above that may be added to the dosage form to assist in satisfactory processing of the dosage form or provide desirable physical characteristics to the dosage form. For example, "pharmaceutically acceptable carriers" may include, but is not limited to, binders, diluents, lubricants, glidants, colorants, emulsifiers, disintegrants, starches, water, oils, alcohols, preservatives, and sugars.

The term "dosage form," as used herein, may be the form in which the dose is to be administered to the subject or patient. The drug or supplement is generally administered as part of a formulation that includes nonmedical agents. The dosage form has unique physical and pharmaceutical characteristics. Dosage forms, for example, may be solid, liquid or gaseous. "Dosage forms," may include for example, a capsule, tablet, caplet, a soft shell capsule, such as a gel caplet (gel-cap), syrup, a liquid composition, a powder, a concentrated powder, a concentrated powder admixed with a liquid, a chewable form, a swallowable form, a dissolvable form, a water soluble film, an effervescent, a granulated form, a pellet form, and an oral liquid solution. Dosage forms may also include a subdermal implant, transdermal patch, injectable form, nasal spray, adhesive tablets, or transmucosally delivered solutions.

As used herein, the terms "inactive," "inert," "excipient," and/or "formulatory" refer to any compound that is an inactive ingredient of a described composition. The definition of "inactive ingredient" as used herein follows that of the U.S. Food and Drug Administration, as defined in 21 C.F.R. § 201.3(b)(8), which is any component of a drug product other than the active ingredient.

The term "active ingredient," then, includes any compound intended to furnish pharmacological activity or other direct effect in the diagnosis, cure, mitigation, treatment and/or prevention of disease or a condition. See 21 C.F.R. § 210.3(b)(7). Further, "active ingredients" include those compounds of the composition that may undergo chemical change during the manufacture of the composition and be present in the final composition in a modified form intended to furnish an activity or effect. Id. In embodiments of the invention, this may include the alpha-1-adrenoreceptor antagonist, (R)-silodosin.

The term "administrable" defines a composition that is able to be given to a subject. Likewise, "administering" refers to the act of giving a composition to a subject or otherwise making such composition available to a subject or the subject taking a composition.

The term "aspermia" refers to failure to produce semen, or absence of sperm in the semen.

The term "azoospermia" refers to the absence of viable sperm in the semen.

The term "severe oligozoospermia" refers to a low count of sperm in ejaculate, typically about less than or equal to $1\times10^6$ sperm per ejaculate.

The term "male contraception" refers to a method used on males to prevent pregnancy of their female sexual partners. It may refer to including one of the conditions of aspermia, azoospermia, or severe oligozoospermia in such a manner that makes the male subject unable to impregnate.

The term "Multiparticulate" means comprise more than one particle, term particle meaning a sphere, a microsphere, a tablet, a microtablet, a capsule or a microcapsule. The term multiparticulate may include clustered, pelletized, compressed or loose particles.

The term "Once-a-day administration" means about the same time i.e. more or less 2 hours.

As used herein, the term "contraceptive efficacy" or "contraceptively effective" refers to the function of a treatment as described herein for inducing reversible aspermia, azoospermia or severe oligozoospermia in which a male subject's ejaculate is incapable of inducing pregnancy through sexual contact in a female sexual partner. Accordingly, the term "sufficient for contraceptive effect," when used, e.g., in reference to a treatment regimen or an amount of a drug or formulation, refers to a treatment that renders a male subject's ejaculate incapable of inducing pregnancy through sexual contact in a female sexual partner. "Interrupting" contraceptive efficacy refers to the return of a male subject's capacity to impregnate a female sexual partner through sexual contact.

A treatment regimen using once-daily doses of an alpha-1-adrenoreceptor antagonist as described herein establishes a reversible condition or state of aspermia, azoospermia or severe oligozoospermia in a male subject that is sufficient for contraceptive effect and continuous as long as once-daily doses are administered, preferably, for example, at about the same time each day. As used herein, the term "does not affect the continuous state of aspermia, azoospermia or severe oligozoospermia sufficient for contraceptive effect," when used in reference to failure to administer one or more daily doses of a formulation as described herein, e.g., after an initial period of regular dosing sufficient for contraceptive effect, means that the failure to administer a given dose or doses over a given span of time after contraceptive efficacy is established does not interrupt the contraceptive efficacy of the treatment over that span of time.

As used herein, the term "short term" treatment refers to a treatment regimen of at least 8 days of daily doses, generally not exceeding 20 days. Short term treatment, as the term is used herein, can encompass one or more missed daily doses after an initial period of regular dosing sufficient to establish contraceptive effect. "Long term" treatment is treatment for greater than 20 days, including, for example, 30 days/one month, 45 days, 60 days/two months, three months, four months, five months, six months, seven months, eight months, nine months, ten months, eleven months, one year or more, e.g., two years, three years or more. Long term treatment, as the term is used herein, can encompass treatment including one or more occasional missed daily doses.

As used herein, the term "orthostatic hypotension" refers to a systolic blood pressure decrease of at least 20 mm Hg or a diastolic blood pressure decrease of at least 10 mm Hg within three minutes of standing.

Oral contraceptives for female subjects are well known in the art such as, for example, Loestrin®, Natazia®, Ortho-Novum®, Ortho Tri-Cyclen®, Yasmin® and Yaz®. Other hormonal contraceptives may be administered to female patients through other dosage forms or methods, such as injection (e.g., Depo-Provera®), transdermal patch (e.g., Ortho Evra®), subdermal implant (e.g., Nexplanon®), vaginal ring (e.g., Nuva-Ring®) or intrauterine device (e.g., Mirena®). No comparable commercial contraceptive product (either hormonal or non-hormonal) is available to male subjects.

This invention relates to the use of a composition in a non-hormonal contraception method for a male subject, the composition comprising an alpha-1-adrenoreceptor antagonist, preferably an alpha-1a-adrenoreceptor antagonist, more preferably silodosin; and a pharmaceutically acceptable carrier. The non-hormonal contraception method includes a once-a-day administration of the composition according to the present invention. In order to maintain an effective exposure to the male subject, the contraception method is carried out for at least two days.

This once-a-day administration induces a contraceptive effect resulting from triggering aspermia, azoospermia, or severe oligozoospermia in the male subject for at least 24 hours.

In another aspect, the invention relates to a method for male contraception. This method comprises the administration of a composition comprising an alpha-1-adrenoreceptor antagonist; and a pharmaceutically acceptable carrier, wherein the composition has a contraceptive effect by inducing aspermia, azoospermia or severe oligozoospermia making the male subject unable to conceive.

In another aspect, the invention relates to a method for inducing a continuous state of aspermia, azoospermia, or severe oligozoospermia in a male subject. This method comprises the administration of a composition comprising an alpha-1-adrenoreceptor antagonist; and a pharmaceutically acceptable carrier. In such aspects, the alpha-1-adrenoreceptor antagonist, compositions and formulations thereof, as well as the frequency of the administration can be as previously described.

Advantageously, the contraceptive effect obtained by the once-a-day administration of the composition of the invention is not affected by a delay of the consecutive once-a-day administration, supposed to occur 24 hours after the former administration, said delay not exceeding 6 hours after first administration, and said delay not exceeding 24 hours after further administration. Thus, the contraceptive effect obtained by the once-a-day administration of the composition of the invention is not reversed by a delay of the consecutive once-a-day administration, said delay not exceeding 6 hours after first administration, and said delay not exceeding 24 hours after further administration.

In a particular embodiment, the daily administration of the alpha-1-adrenoreceptor antagonist is made at about the same time on each day. In this particular embodiment, about means two hours before or after the same time.

A regular timetable in the administration has the benefit of assisting with patient compliance with the daily administration schedule. Further, as discussed in more detail below, for contraceptive products, it is usually recommended to take the drug at approximately the same time each day in order to maintain an effective exposure of the patient to the drug all along the dosing interval. According to one embodiment, the daily administration contraception method is a single daily administration contraception method. The non-hormonal contraceptive compositions described herein may include any alpha-1-adrenoreceptor antagonist. A person skilled in the art can adapt the composition using his general knowledge on the pharmacodynamic and pharmacokinetic properties of the said alpha-1-adrenoreceptor antagonist. In one embodiment, the alpha-1-adrenoreceptor antagonist is selected from the group comprising silodosin, terazosin, doxazosin, tamsulosin and fiduxosin.

In a preferred embodiment, the composition implemented in the present invention comprises silodosin as an alpha-1-adrenoreceptor antagonist. In another embodiment, the composition comprises tamsulosine as an alpha-1-adrenoreceptor antagonist.

In a preferred embodiment, the alpha-1-adrenoreceptor antagonist is (R)-Silodosin. (R)-Silodosin, formally known as (−)-(R)-1-(3-hydroxypropyl)-5-[2-[[2-[2-(2,2,2-trifluoroethoxy)phenoxy]ethyl]amino]propyl]indoline-7-carboxamide ("(R)-Silodosin"). The molecular formula is $C_{25}H_{32}F_3N_3O_4$, and it has a molecular weight of 495.53. (R)-Silodosin has the chemical structure shown below:

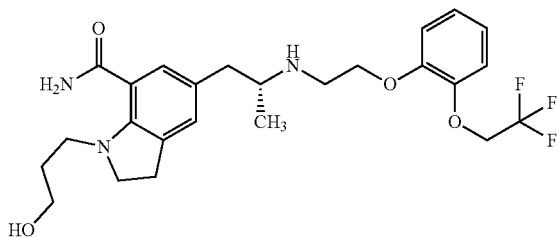 [SMILES: C[C@H](Cc1cc2c(c(C(N)=O)c1)N(CCCO)CC2)NCCOc1ccccc1OCC(F)(F)F]

Silodosin is powder that appears white or pale yellow/white. It melts at approximately 105 to 109° C. It is very soluble in acetic acid, freely soluble in alcohol, and very slightly soluble in water. In one embodiment, the alpha-1-adrenoreceptor antagonist is (R)-Silodosin in a polymorphic or amorphous form In embodiments of the invention, (R)-Silodosin may be particularly advantageous because it is a known antagonist of the alpha-1a-adrenoreceptors, and particularly, has high affinity and selectivity toward human alpha-1-adrenoreceptors is high (pKi=10.4±0.07) (CDER, NDA 22-206, PHARMACOLOGY REVIEWS. September 2008).

The ejaculatory process is mainly mediated by the autonomic nervous system and consists of two main phases: emission and expulsion. Two groups of anatomical structures are specifically involved and distinguished in each phase. The organs involved in the emission phase comprise the epididymis, vas deferens, seminal vesicles, prostate gland, prostatic urethra and bladder neck. The organs participating in the expulsion phase include the bladder neck and urethra, as well as the pelvic striated muscles.

The first phase is the emission phase. During the emission phase, spermatozoa mixed with products secreted by accessory sexual glands are ejected into the posterior urethra by sequential epithelial secretion and smooth muscle cell contractions. The second phase is the expulsion phase. During the expulsion phase, sperm is ejected from the urethra through the glans meatus. According to the commonly accepted theory, expulsion is a spinal cord reflex that occurs as the ejaculatory process reaches its peak. It involves closure of bladder neck, followed by the rhythmic contractions of the urethra by pelvic-perineal and bulbospongiosus muscle, and intermittent relaxation of external urethral sphincters.

Sympathetic motor neurons control the emission phase of ejaculation reflex, and expulsion phase is executed by somatic and autonomic motor neurons. These motor neurons are located in the thoracolumbar and lumbosacral spinal cord and are activated in a coordinated manner when sufficient sensory input to reach the ejaculatory threshold has entered the central nervous system. Lumbar spinothalamic (LSt) cells have been described as the spinal ejaculation generator in animals.

Transportation of spermatozoa from their storage sites in the cauda epididymis via the vas deferens and in the seminal vesicles to the urethra is understood to be blocked by silodosin. This process of propulsion of sperm into the ejaculate is essential for males to produce an adequate sperm count for fertilization. Sympathetically innervated smooth muscle cells surround the vas deferens and seminal vesicles and contract in response to noradrenaline due to activation of α1A-adrenergic G protein-coupled receptors (adrenoceptors, or "AR"). Sympathetically mediated sperm transport is thereby blocked through the vas deferens during the emission phase of ejaculation, producing infertility without effects on sexual behavior or function.

The ejaculatory reflex is not modified by silodosin as the sensory inputs from genital and brain areas to the spinal generator of ejaculation (lumbospinothalamic, or "LSt") neurons) remain intact. The spinal generator role and function are not modified by silodosin as LSt cells are not known to have adrenergic receptors, only neurokinin and galanin receptors (Coolen et al PHYSIOL BEHAV, 2004, 83(2), 203-215).

Accordingly, the non-hormonal contraceptive compositions of the present invention do not impact the production of semen in a male subject. Instead, they regulate the transport out of the semen and spermatozoa. This is advantageous over more permanent contraception methods (i.e., a vasectomy) because it is reversible upon cessation of administration of the drug.

Embodiments of the invention may be, include, or resemble a variety of dosage forms that are well known in the art. For example, this may include capsules, tablets, caplets, soft shell capsules, gel caplets (gel-caps), syrups, liquid compositions, powders, concentrated powders, concentrated powders admixed with liquids, chewable forms, swallowable forms, dissolvable forms, water soluble films, effervescents, granulated forms, pellet forms, and oral liquid solutions. In a particular embodiment of the invention, the dosage form may comprise microgranules in a hard capsule containing a pharmaceutically effective amount of (R)-Silodosin to guarantee the contraceptive efficacy during a targeted duration. In such an embodiment, the microgranules may comprise (i) an inert core, (ii) a drug layer applied to the inert core, comprising (R)-Silodosin and a binder, and (iii) a controlled release coating surrounding the drug layer. Further embodiments of the invention may also comprise, optionally, a surfactant in combination with item (ii). A hard capsule may then be filled with the microgranules. Additionally or alternatively, the microgranules may be matrix microgranules of (R)-Silodosin surrounded by controlled release coating and filled in a hard capsule. Alternatively, the granules can be compressed into a tablet. The compositions described in this paragraph, including methods for preparing them, are well known in the pharmaceutical arts. WADE & WELLER, HANDBOOK OF PHARMACEUTICAL EXCIPIENTS (2nd ed. 1994); REMINGTON: THE SCIENCE AND PRACTICE OF PHARMACY (21st ed. 2005).

The composition can be into a single day oral dosage forms selected from the group consisting of: soft-gels, caplets, pills, tablets, microtablets, capsules, hydromatrix tablets, and osmotic tablets.

Embodiments of the invention may further be, include, or resemble microtablets in a hard capsule, a coated tablet, a hydromatrix tablet, or an osmotic tablet containing a pharmaceutically appropriate amount of (R)-Silodosin to guarantee the contraceptive efficacy during a targeted duration. Embodiments of the invention may therefore comprise microtablets, specifically, matrix tablets of (R)-Silodosin surrounded by controlled release coating, and filled in a hard capsule. The tablets can optionally be coated by a controlled release coating prior to their formulation into a tablet. A coated tablet may be or comprise a matrix tablet of (R)-Silodosin surrounded by controlled release coating. A coated tablet may be or comprise a matrix tablet of the alpha-1-adrenoreceptor antagonist surrounded by controlled release coating. In embodiments of the invention, a hydromatrix tablet may also be used as a dosage form, particularly, e.g., a single or multiple-layer tablet comprising alpha-1-adrenoreceptor antagonist or (R)-Silodosin and an hydrophilic excipient. The compositions described in this paragraph, including methods for preparing them, are well known in the pharmaceutical arts. See e.g., Peter Timmins et al., Hydrophilic Matrix Tablets for Oral Controlled Release (2014); Rumondor et al., Minitablets: Manufacturing, Characterization Methods, and Future Opportunities. Jul. 30, 2016; Nokhodchi A., *The Role of Oral Controlled Release Matrix Tablets in Drug Delivery Systems,* 2(4) BIOIMPACTS, 175-187 (2012).

In such embodiment, the compositions administrated in the use according to the present invention are formulated in forms comprising granules or tablets. The granules or tablets may optionally be coated by a controlled release coating.

The granules or tablets, as previously described, can be further filled into a capsule that optionally comprises a controlled release coating.

In one embodiment, the composition is in a multiparticulate form. In such embodiment, a capsule may then be filled with the previously described particles or granules. The sufficient number of these particles or granules within the capsule is determined by a person skilled in the art in view of reaching to daily dose of the alpha-1-adrenoreceptor antagonist.

In one embodiment, the contraceptive effect resulting from triggering aspermia, azoospermia, or severe oligozoospermia and the absence of undesired side effects in the male subject is achieved independently from the food consumption by the male subject.

In one embodiment, contraceptive effect resulting from triggering aspermia, azoospermia, or severe oligozoospermia in the male subject has the same efficacy and/or safety profile independently from the food consumption by the male subject.

In one embodiment, the composition comprising the alpha-1-adrenoreceptor antagonist includes or consists of at least one particle, preferably at least one coated particle, and the average particle diameter is in the range of 0.01 to 5 mm, preferably 0.1 to 2 mm.

The present invention, however, is not limited to oral administration of, e.g., capsules, tablets, and the like. Embodiments of the invention may be or comprise other dosage forms or methods, such as injection, transdermal patch, or subdermal implant. These are also well known in the arts and in embodiments of the invention may be similar to comparable female contraceptive products, such as, for example, Depo-Provera®, Ortho Evra®, and Nexplanon®, respectively.

The therapeutic dose of (R)-Silodosin used in any of the dosage forms described or referred to herein may be or include, by way of example only, about 4 mg, about 8 mg, about 12 mg, about 16 mg, or about 20 mg. It is known in the art that one of the main side effects of alpha blockers is orthostatic hypotension (Roehrborn C. *Alpha1-Blockers in Men with Lower Urinary Tract Symptoms Suggestive of Benign Prostatic Obstruction: Is Silodosin Different?* ADV THER (2016) 33:2110-2121). It is well accepted that these side effects, and particularly orthostatic hypotension, are dose-dependent and related to the maximum (or peak) serum concentration of the drug in plasma ($C_{max}$). This is illustrated by, for example, the fact that health authorities recommend that the alpha-1 blockers tamsulosin and (R)-Silodosin are taken with food in order to decrease the peak of their plasma concentration and consequently limit the occurrence of the cardiovascular side effects. Preclinical animal data are also very supportive of the relationship between the plasma $C_{max}$ of alpha-1 blockers and their cardiovascular side effects (Hancock A, et al. *Preclinical Pharmacology of Fiduxosin, a Novel α1-Adrenoceptor Antagonist with Uroselective Properties*. JPET (2002) 300: 478-486).

In embodiments of the invention, the non-hormonal contraceptive compositions are administered to a male subject once daily. This has the benefit of assisting with patient compliance with the daily administration schedule (M. Rosenberg et al. *Compliance, Counseling and Satisfaction with Oral Contraceptives: A Prospective Evaluation*. PERSP. ON SEX. & REPROD. HEALTH. 1998, 30(2), 89-92). Further, as discussed in more detail below, for pharmaceutical products that are dosed in this manner, it is usually recommended to take the drug at approximately the same time each day in order to maintain an effective exposure of the patient to the drug all along the dosing interval. Such a regimen may also be recommended for (R)-Silodosin (Recordati Ireland Limited. *Urorec summary of product characteristics*. Updated June 2015).

Current formulations of (R)-Silodosin for the treatment of BPH, such as the commercial product Rapaflo®, release the active ingredient immediately upon swallowing, and thus are "immediate release" (or "IR") formulations. For a contraceptive product, however, embodiments of the invention comprising a formulation of the non-hormonal contraceptive compositions in which the therapeutic effect is capable of withstanding a delay in intake may be particularly desirable. Such formulations may be referred to as an "extended release" (or "ER") formula. In such embodiments, a male subject's delay in intake, or failure to intake, one (or more) dose(s) would not nullify the contraceptive effect of the treatment regimen, and would also allow a day-to-day adjustment of a more convenient intake time.

For an extended release formulation intended for once daily administration to a male subject, while allowing for delays and/or omissions in administration, the therapeutic dose should be adjusted in embodiments of the invention to maintain an effective control of sperm ejaculation.

For instance, and by way of example only, the contraceptive effect may be designed to withstand a delay of 6 hours (e.g., contraceptive effect maintained up to 24 hours, and an additional six hour delay, for a total of 30 hours post-dose) once the steady state is reached in a male subject. In embodiments of the invention, this duration of action is longer and/or faster acting, and may be reached from one, two, three, four, five, or six initial doses. It should be noted the typical means of achieving a lengthening of the duration of action—an increase of the therapeutic dose—is not a viable option in the case of (R)-Silodosin, as it would expose the patient to a significant increase in the risk of orthostatic hypotension.

According to a first embodiment, the daily administration of the alpha-1-adrenoceptor antagonist can be delayed as of the third day of two consecutive daily intakes with no impact on the contraceptive effect on the male subject, such delay not exceeding 2, 4, 6, 8, 10 12, 16, 20 or 24 hours from the day-before uptake time, preferably not exceeding 2, 4, 6 hours from the day-before uptake time.

According to second embodiment, the daily administration of the alpha-1-adrenoceptor antagonist can be delayed as of the fourth day of three consecutive daily intakes with no impact on the contraceptive effect on the male subject, such delay not exceeding 2, 4, 6, 8, 10 12, 16, 20 or 24 hours from the day-before uptake time.

According to a third embodiment, the daily administration of the alpha-1-adrenoceptor antagonist can be delayed as of the fifth day of four consecutive daily intakes with no impact on the contraceptive effect on the male subject, such delay not exceeding 2, 4, 6, 8, 10 12, 16, 20 or 24 hours from the day-before uptake time.

According to a fourth embodiment, the daily administration of the alpha-1-adrenoceptor antagonist can be delayed as of the sixth day of five consecutive daily intakes with no impact on the contraceptive effect on the male subject, such delay not exceeding 2, 4, 6, 8, 10 12, 16, 20 or 24 hours from the day-before uptake time.

According to a fifth embodiment, the daily administration of the alpha-1-adrenoceptor antagonist can be delayed as of the seventh day of six consecutive daily intakes with no impact on the contraceptive effect on the male subject, such delay not exceeding 2, 4, 6, 8, 10 12, 16, 20 or 24 hours from the day-before uptake time.

In one embodiment, the once-a-day administration contraception method is carried out for at least two days. In one embodiment, the once-a-day administration contraception method is carried out for at least three days. In one embodiment, the once-a-day administration contraception method is carried out for at least for at least four days. In one embodiment, the once-a-day administration contraception method is carried out for at least for at least five. In one embodiment, the once-a-day administration contraception method is carried out for at least six days.

According to the aforementioned embodiments the delay of a subsequent daily administration does not exceed 2, 4, 6, 8, 10 12, 16, 20 or 24 hours from the day-before uptake time. In one embodiment, the delay does not exceed 2, 4, 6, 8, 10 12, 16, 20 or 24 hours from the day-before uptake time. In one embodiment, the delay does not exceed 2 hours from the day-before uptake time. In one embodiment, the delay does not exceed 4 hours from the day-before uptake time. In one embodiment, the delay does not exceed 6 hours from the day-before uptake time. In one embodiment, the delay does not exceed 8 hours from the day-before uptake time. In one embodiment, the delay does not exceed 10 hours from the day-before uptake time. In one embodiment, the delay does not exceed 12 hours from the day-before uptake time. In one embodiment, the delay does not exceed 16 hours from the day-before uptake time. In one embodiment, the delay does not exceed 20 hours from the day-before uptake time. In one embodiment, the delay does not exceed 24 hours from the day-before uptake time.

In one embodiment, the dosage form is self-administered.

Therefore, embodiments of the invention comprise modification of the pharmacokinetic profile of (R)-Silodosin in such a way that, at the steady state, Its $C_{max}$ is lowered compared to the pharmacokinetic profile obtained with the IR and/or other traditional formulations of (R)-Silodosin. In embodiments of the invention, the $C_{max}$ of an ER formulation of (R)-Silodosin is lower than the $C_{max}$ reached with the same dose administered in the IR and/or other traditional formulation, leading to a lower risk of orthostatic hypotension. In further embodiments of the invention, this also means that the $C_{max}$ of IR/traditional (R)-Silodosin and the $C_{max}$ reached with a higher dose administered in the ER formulation may be comparable, allowing an additional therapeutic effect without an increased risk of orthostatic hypotension.

In embodiments of the extended release formulation described herein, the non-hormonal compositions may also allow for consumption with or without food. Typically, as discussed herein, alpha-1 blockers are administered with food in order to decrease the peak of their plasma concentration and consequently limit the occurrence of the cardiovascular side effects. A so-called "food effect" is known to impact the pharmacokinetic profile of traditional formulations of (R)-Silodosin, leading to a delayed $T_{max}$ and lower $C_{max}$. (EMA/793234/2009. CHMP assessment report for Urorec. Procedure No. EMEA/H/C/001092. 10 Jan. 2010.) It is assumed that these effects are due to the delayed voiding of the stomach in the presence of food.

As described above, embodiments of the invention may comprise unitary dosage forms such as microgranules or microtablets in hard capsule that are released in the stomach. With sufficiently small size (for instance, e.g., with a diameter ≤5 mm, preferably ≤2 mm) to progress to the intestine in the flow of the digestive fluids, microgranules or microtablets will not be retained in the stomach with the food. Thus, the food effect—which relies upon a delayed voiding of the stomach in the presence of food—would not impact such formulations. Notably, additional mechanisms may be responsible for avoidance of the food effect.

In embodiments of the invention, the microgranules or microtablets may also be designed with a specific density in order to avoid the food effect. If the density of the microgranules or microtablets is too low, they will float at the top of the gastric fluids contained in the stomach during a fasting state, delaying transit to the intestine. Accordingly, in embodiments of the invention, the target density of the microgranules or microtablets may be designed to avoid the floating phenomenon. In embodiments of the invention, a density ≥1 may be desirable. In embodiments of the invention, a density ranging from about 1 to about 1.6 may be desirable. However, those skilled in the art will appreciate that other densities may be appropriate or ideal.

As previously discussed, male orgasm is controlled by the involuntary, or autonomic, limbic nervous system and occurs in the pleasure centers in the brain. During orgasm, the anterior lobe of the cerebellar vermis and deep cerebellar nuclei are activated; the left ventromedial and orbitofrontal cortex are de-activated.

Although no effect of silodosin has been described on central nervous pathways, and it is possible for patients on silodosin administration to still experience orgasms, as reported by Shimizu et al. However, some studies have reported a decrease in orgasmic quality for male subjects who are administered silodosin daily, including Shimizu et al and Capogrosso et al., while others, including Kobayashi et al. and Bozkurt et al., have reported discomfort upon ejaculation.

Embodiments of the invention therefore include methods and compositions of administering silodosin which do not significantly impair the quality of orgasm for the male subject (often measured by the Numerical Rating Scale, NRS, for the quality of orgasm). Other potential side effects which the claimed invention would avoid (or, at minimum, maintain) are decreased sexual desire, feelings of reduced virility, ejaculation distress, decreased satisfaction, undesirable decrease or increase in intravaginal ejaculation latency time, and/or premature ejaculation.

In embodiments of the invention, silodosin is either present alone, or in association with another active agent, or in combination with another active agent. The non-hormonal contraceptive compositions of the present invention.

In an embodiment of the invention, alpha-1-adrenoreceptor antagonist, preferably silodosin may be included or used in the non-hormonal contraceptive compositions in any specific form just described. In another embodiment, the non-hormonal contraceptive compositions may include or use a combination of alpha-1-adrenoreceptor antagonist or other components in the ranges or amounts just described.

In a specific embodiment, various active ingredients may be incorporated into multiple compositions as a kit. In some embodiments, the non-hormonal contraceptive compositions disclosed herein may be packaged as kits using materials known to those of ordinary skill in the art.

In one embodiment, the use of the composition in the daily administration contraception method further comprises a simultaneous or sequential administration of an additional composition. In one embodiment, the additional composition is related or not related to the sexual health of the male subject. In one embodiment, the additional composition does not affect the cardiovascular system of the male subject. In one other embodiment, the additional composition affects the cardiovascular system of the male subject. More in particular, the additional composition may induce the lowering of the male subject arterial pressure.

Advantageously, the safety profile of the present inventions male contraceptive method allows the simultaneous or sequential administration of an additional composition that may lower the patient's arterial pressure, with no risk of a hypotensive crisis.

Phosphodiesterase type 5 (PDE5) inhibitors, for example, are a class of drugs used in the treatment of erectile dysfunction. Because the prevalence of erectile dysfunction and of BPH increases in aging men, embodiments of the invention may comprise the co-administration of PDE5 inhibitors and (R)-Silodosin in male patients suffering from both pathologies.

In one embodiment, use of the composition in the daily administration contraception method further comprises a simultaneous or sequential administration of an additional composition suitable for treating erectile dysfunction; preferably the additional composition comprises a phosphodiesterase-5 inhibitor.

PDE5 inhibitors are mild vasodilators associated with small decreases in blood pressure. (Huang S; and Lie J. *Phosphodiesterase-5 (PDE5) Inhibitors In the Management of Erectile Dysfunction*. PT (2013) 38(7): 407, 414-419.) Alpha-blockers are also well known vasoactive compounds. Thus, the co-administration of PDE5 inhibitors and alpha-blockers may, under some circumstances, result in additive vasodilatory effect, particularly within patient populations likely to be prescribed PDE5 inhibitors in clinical practice. (Schwartz B, Kloner R. *Drug Interactions With Phosphodiesterase-5 Inhibitors Used for the Treatment of Erectile Dysfunction or Pulmonary Hypertension*. CIRCULATION (2010) 122:88-95) (CDER, NDA 22-206, Medical Reviews, September 2008.) However, the embodiments of the invention described herein can include an ER (R)-Silodosin formulation with a decreased alpha blocker $C_{max}$. Because the cardiovascular side effects of alpha blockers are partially related to the $C_{max}$, this would likely minimize the potential for additive side effects during co-administration of PDE5 inhibitors.

Another typical way to limit the risk of side effects of co-administration of an alpha blocker and PDE5 inhibitor is to separate the intake of each drug by several hours, as reported by Schwartz et al. The median $T_{max}$ (time when the peak of plasma concentrations are reached) of the 4 currently marketed PDE-5 inhibitors (sildenafil, vardenafil, tadalafil, avanafil) ranges from 0.5 to 2 hours (Sharon A. Huang; and Janette D. Lie. *Phosphodiesterase-5 (PDE5) Inhibitors In the Management of Erectile Dysfunction*. P&T (2013) 38 (7):407-419). The median $T_{max}$ of (R)-Silodosin is about 2 hours. Center for Drug Evaluation and Research, NDA 22-206, *CLINICAL PHARMACOLOGY AND BIO-PHARMACEUTICS REVIEWS* (July 2008). When the alpha blocker and the PDE-5 inhibitor are taken several hours apart, the $C_{max}$ of each compound is not reached in the same time so that the cumulative effect is lower. However, as described herein, in embodiments of the present invention, such as an ER formulation of (R)-Silodosin, the $C_{max}$ is lower than in traditional/IR formulations of (R)-Silodosin and the $T_{max}$ is delayed further apart from the $T_{max}$ of its associated PDE5 inhibitor. Thus, it is possible to co-administer an alpha blocker composition as described herein as well as the PDE-5 inhibitor in the same time.

Advantageously, alpha-adrenoreceptor antagonist extended release formulations allow the simultaneous or sequential administration of an additional composition that may lower the patient's arterial pressure, with no risk of a hypotensive crisis. In one embodiment, the alpha-adrenoreceptor antagonist is an alpha-1-adrenoreceptor antagonist, preferably (R)-Silodosin. In one embodiment, the extended release formulations are adapted according to the general knowledge of the skilled artisan. In one embodiment the extended release formulations are the extended release formulations according to the present invention The kits of the present invention may comprise or use a combination of compositions, including but not limited to PDE5 inhibitors. Additionally or alternatively, kits may further include, by way of example, one or more back-up methods of birth control provided in the event that it is needed. For instance, embodiments of the invention may comprise a composition formulated to maintain a contraceptive effect in a male subject for about 30 hours. If the male subject engages in sexual intercourse after about 30 hours, it may be necessary or optimal to utilize a back-up method of birth control, such as a condom or an emergency contraceptive such as, e.g., Plan B One-Step® or EllaOne.

In embodiments of the invention, the kit may be packaged in a sachet or package. In such embodiments, a kit may comprise one or more individual dosage forms. In some embodiments, each kit may comprise two individual dosage forms. In some embodiments, each kit may comprise three individual dosage forms. In some embodiments, a kit may comprise a total dosage form.

Additionally or alternatively, in embodiments of the invention, an individual dosage form, unit dosage form, or total dosage form may be individually wrapped, packaged as multiple units on paper strips or in vials of any size, without limitation. The orally dissolvable compositions of the invention may be packaged in unit dose, rolls, bulk bottles, blister packs, and combinations thereof, without limitation.

Therefore, the invention also relates to a packaging of unitary doses of the composition of the invention. The composition, as previously described, includes alpha-1-adrenoreceptor antagonist in an amount ranging from about 0.1 to about 30 mg, preferably from about 0.2 to about 20 mg, preferably the alpha-1-adrenoreceptor antagonist is (R)-silodosin in an amount of 8 to 12 mg.

In one embodiment the male contraceptive packaging comprises at least one packaging unit; wherein said packaging unit comprises from about 7 to about 30 separately packaged unitary doses of the composition as described in the present invention.

In one embodiment, the male contraceptive packaging comprises from about 7 to about 28 unitary doses. The male contraceptive packaging may comprise 7, 14, 28, 56 or 84 unitary doses. The male contraceptive packaging may be suitable for longer periods of the non-hormonal male contraception method of the present invention. In such embodiments, the male contraceptive packaging comprises 7, 14, 28, 56, 84 or 168 to 365 unitary doses of the composition as described in the present invention.

According to another embodiment the male contraceptive packaging comprises from about 10 to about 30 unitary doses. The male contraceptive packaging may comprise 10, 20, 30, 60 or 90 unitary doses. The male contraceptive packaging may be suitable for longer periods of the non-hormonal male contraception method of the present invention. In such embodiments, the male contraceptive packaging comprises 10, 20, 30, 60, 90 or 180 to 360 unitary doses of the composition as described in the present invention.

In one embodiment the unitary doses are placed in at least one blister. The male contraceptive packaging is adequately labeled and may further comprise instructions for the male contraception method according to the present invention.

All pharmaceutical preparations described herein are well known to those of ordinary skill in the art, and determination of workable methods for preparing orally dissolvable compositions in any particular instance will generally be within the capability of the person skilled in the art.

Details concerning any of excipients may be found in WADE & WELLER, *HANDBOOK OF PHARMACEUTICAL EXCIPIENTS* (2nd ed. 1994). AU active ingredients, fillers and excipients are commercially available from companies such as Aldrich Chemical Co., FMC Corp, Bayer, BASF, Alexi Fres, Witco, Mallinckrodt, Rhodia, ISP, and others. The excipients used in the orally dissolvable compositions fall into several functional categories and may include, by way of example, plasticizers, emulsifiers, taste enhancers, sweeteners, and flavoring agents. Additionally or alternatively, excipients may be of the type used in other FDA-approved oral contraceptive products.

In one embodiment, the non-hormonal contraceptive compositions comprise one or more inactive ingredients. The inactive ingredients may comprise one or more of the following: sugar, corn syrup, water, gelatin, citric acid, lactic acid, one or more glazing agents (e.g., vegetable oil, beeswax, carnauba wax), one or more natural flavors (e.g., plum, apple, mixed berry, cherry), one or more natural colors (e.g., black carrot), and one or more masking flavors (e.g., tartaric acid, menthol).

In some embodiments, the non-hormonal contraceptive compositions may comprise one or more inactive ingredients that include but are not limited to water, buffers (including, by way of example and without limitation, phosphate buffers, citrate buffers, lactic acid, and others known to those of ordinary skill in the art), stabilizing agents (including, by way of example and without limitation, antioxidants (e.g., ascorbic acid, propionic acid, sodium bisulfite, sodium sulfite, and the like), chelating agents (e.g., fumaric acid, sodium edetate, and the like), and others known to those of ordinary skill in the art), surfactants (including, by way of example and without limitation, wetting agents (e.g., sorbitan monolaurate, etc.), antifoaming agents (e.g., sorbitan trioleate, etc.), detergents (e.g., sucrose stearate, etc.), solubilizing agents (e.g., polyethylene glycol 400 monostearate, etc.), and others known to those of ordinary skill in the art), processing aids (e.g., substances used to assist processing, including, by way of example and without limitation, lubricating agents, antioxidants, and others known to those of ordinary skill in the art), lubricating agents (including, by way of example and without limitation, stearic acid, calcium stearate, magnesium stearate, zinc stearate, talc, mineral and vegetable oils, benzoic acid, poly (ethylene glycol), glyceryl behenate, stearyl fumarate, and others known to those of ordinary skill in the art), emulsifiers (including, by way of example and without limitation, synthetic (e.g., sodium lauryl sulfate, potassium laurate, etc.), natural (e.g., gelatin, lecithin, etc.), and finely divided solid emulsifiers (e.g., bentonite, magnesium hydroxide, etc.), and others known to those of ordinary skill in the art), suspending agents (including, by way of example and without limitation, cellulose derivatives (e.g., carboxymethylcellulose, methylcellulose, ethyl cellulose, etc.), natural polymers (e.g., alginates, xanthan gum, guar gum, etc.), synthetic polymers (e.g., carbomers, polyvinyl pyrrolidone, etc.), clays (e.g., magnesium aluminum silicate, hectorite, etc.), and others known to those of ordinary skill in the art), preservatives (including, by way of example and without limitation, benzalkonium chloride, benzethonium chloride, benzyl alcohol, cetrimide, glycerin, propylene glycol, benzoic acid and sodium benzoate, potassium sorbate and sorbic acid, and others known to those of ordinary skill in the art), opaquing agents (including, by way of example and without limitation, titanium dioxide, and others known to those of ordinary skill in the art), glidants (including, by way of example and without limitation, silicon dioxide, colloidal or fumed silica, magnesium stearate, calcium stearate, stearic acid, cornstarch, talc and others known to those of ordinary skill in the art), diluents (including, by way of example and without limitation, corn syrup, lactose, sodium chloride, sucrose (sugar), and others known to those of ordinary skill in the art), colorants or coloring agents (including, by way of example and without limitation, FD&C Red No. 3, FD&C Red No. 20, FD&C Yellow No. 6, FD&C Blue No. 2, D&C Green No. 5, FD&C Orange No. 5, FD&C Red No. 8, caramel, ferric oxide, pigments, dyes, tints, titanium dioxide, natural coloring agents, such as grape skin extract, red beet powder, beta carotene, annatto, carmine, turmeric, paprika, black carrot juice, and others known to those of ordinary skill in the art), sweeteners or sweetening agents (including, by way of example and without limitation, sucrose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art), perfuming agents (including, by way of example and without limitation, natural flavor oil, a synthetic flavor oil, and others known to those of ordinary skill in the art), glazing agents (including, by way of example and without limitation, vegetable oil, beeswax, carnauba wax, and others known to those of ordinary skill in the art), flavoring agents or flavorants (including, by way of example and without limitation, natural flavor oil, synthetic flavor oil, and other masking flavors known to those of ordinary skill in the art), and cooling agents (including, by way of example, N-substituted p-menthane-3-carboxamides, such as N-ethyl p-menthane-3-carboxamide ("WS-3") (Millennium Specialty Chemicals, Jacksonville, Fla.). Additional examples of other inactive ingredients are well known in the art. See, e.g., REMINGTON: THE SCIENCE AND PRACTICE OF PHARMACY (21st ed. 2005).

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLES

Example 1

(R)-Silodosin Extended Release Formulation

This example relates to extended release formulations of (R)-Silodosin.

Controlled release granules of (R)-Silodosin are prepared in accordance with the present invention as follows. (R)-Silodosin is suspended in an aqueous solution of hydroxypropylmethyl cellulose (Opadry©) and potassium phosphate monobasic ($KH_2PO_4$). The composition of the (R)-Silodosin suspension is detailed in table 1.

TABLE 1

| (R)-Silodosin suspension composition | |
|---|---|
| | % w/w |
| Silodosin | 9.60 |
| HPMC (Opadry ©) | 10.00 |
| $KH_2PO_4$ | 0.68 |
| Purified water | 79.72 |

Then, the suspension, under continuous stirring, is sprayed onto inert cores of cellulose spheres and the obtained granules are dried. The composition of the obtained granules is presented in table 2.

TABLE 2

| (R)-Silodosin granules composition | |
|---|---|
| | % w/w |
| Silodosin | 4.36 |
| HPMC (Opadry ©) | 4.54 |
| $KH_2PO_4$ | 0.31 |
| Cellulose microspheres | 90.79 |

An aqueous coating solution containing ethylcellulose (ECD Aquacoat®, 26.67% w/w) and dibutylsebaccate (DBS, 2.0% w/w) is then sprayed onto the (R)-Silodosin granules and dried. The composition of the protected granules is presented in table 3.

TABLE 3

| (R)-Silodosin protected granules composition | |
|---|---|
| | % w/w |
| Silodosin | 4.15 |
| HPMC (Opadry ©) | 4.32 |
| $KH_2PO_4$ | 0.30 |
| Cellulose microspheres | 86.47 |
| Aquacoat ECD/DBS | 4.76 |

The coated granules are further coated by spraying with an aqueous extended release coating solution of ethylcellulose (ECD Aquacoat®, 25.25% w/w), dibutylsebaccate (DBS, 1.89% w/w) and guar gum (0.53% w/w). The extended release granules are dried and their final composition is presented in table 4, hereafter named formulation A.

TABLE 4

(R)-Silodosin formulation A extended release granules composition

| | % w/w |
|---|---|
| Silodosin | 3.32 |
| HPMC (Opadry ©) | 3.46 |
| KH$_2$PO$_4$ | 0.23 |
| Cellulose microspheres | 69.18 |
| Aquacoat ECD/DBS | 3.81 |
| Aquacoat ECD/guar gum/DBS | 20 |

The average particle size was less than 2 mm and the average density thereof was greater than 1

Hard capsules were filled with the adequate quantity of formulation A to a final content of 8 and 12 mg per capsule.

Example 2

(R)-Silodosin Extended Release Dissolution Rate

The dissolution test for comparison of the dissolution rate of (R)-Silodosin from the reference immediate release (Urorec®) formulation and from the experimental extended release formulation A according to example 1 was carried out at 50 rpm in 900 mL of 0.1N HCl solution in a USP type 2 apparatus at 25° C. The results of this comparative dissolution rate are presented in FIG. 1.

The dissolution rate of the extended release formulation is slowed down compared to that of the reference immediate release formulation.

Example 3

Single Administration Contraceptive Effect

A study is undertaken to evaluate the effectiveness of the compositions of the present invention in the treatment of male subjects. The objective of the study is to determine whether oral intake of (R)-Silodosin formulation results in a contraceptive effect.

A total of 7 subjects, aged 18 to 40 years were enrolled in an open-label study. An initial analysis of each subject's semen, collected via masturbation after 3 days of abstinence, is performed by microscopic examination of the fresh semen. Each subject receives one single dose of 12 mg immediate release (R)-Silodosin.

A semen analysis of each subject is conducted 24 hours after the dosing. The analysis shows the results in Table 5 below.

TABLE 5 efficacy of a single dose of 12 mg of (R)-silodosin given in an immediate release (IR) formulation.

| Effect | 24 h (N = 7) |
|---|---|
| Aspermia | 6/7 |
| Azoospermia | 1/7 |
| Total | 7/7 |

As shown in Table 5, administration of the immediate release (R)-Silodosin formulation led to aspermia or azoospermia in 100% of the male subjects.

The study also showed that administration of the composition did not impair the erectile function nor the quality of orgasm in any of the male subjects.

Example 4

Clinical Studies (Extended Release Formulation)

A study is undertaken to evaluate the effectiveness of the compositions of the present invention in the treatment of male subjects. The objective of the study is to demonstrate that oral intake of an extended release (R)-Silodosin formulation results in aspermia or azoospermia up to 30 hours after administration.

An open-labeled study is conducted in 6 subjects aged 18-45 years. An initial analysis of each subject's semen collected via masturbation after 3 days of abstinence by microscopic examination of the fresh semen. A single dose of 12 mg extended release (R)-Silodosin is administered.

A semen analysis of each subject is conducted utilizing the methods described above at thirty hours after the administration.

Administration of the extended release (R)-Silodosin formulation lead to aspermia or azoospermia in 100% of the male subjects up to thirty hours after administration The study also showed that administration of the composition did not impair the erectile function nor the quality of orgasm in any of the male subjects.

Example 5

Clinical Studies (Extended Release Formulation)

A study is undertaken to evaluate the effectiveness of the compositions of the present invention in the treatment of male subjects. The objective of the study is to determine whether oral intake of an extended release (R)-Silodosin formulation results in aspermia or azoospermia.

A double-blind, placebo controlled study is conducted over a two week period. A total of 20 subjects, aged 20-45 years, are chosen for the study. An initial analysis of each subject's semen collected via masturbation after 3 days of abstinence using by microscopic examination of the fresh semen. A single dose of 12 mg extended release (R)-Silodosin is administered daily to each subject for five days.

A semen analysis of each subject is conducted utilizing the methods described above at twelve, twenty-four, thirty-six, and forty-eight hours after the administration of the final dose.

Administration of the extended release (R)-Silodosin formulation lead to aspermia or azoospermia in 100% of the male subjects for twenty-four hours after the fifth and final dose. Further, 100% of the male subjects experienced aspermia or azoospermia for at least forty-eight hours after the fifth and final dose, showing that a missed dose on the sixth day did not impact the efficacy achieved by administration of the composition.

The study also showed that administration of the composition did not impair the erectile function nor the quality of orgasm in any of the male subjects.

Example 6

Clinical Studies (Extended Release Formulation and the Food Effect)

A study is undertaken to evaluate the effectiveness of the compositions of the present invention in the treatment of male subjects when administered in the presence of food. The objective of the study is to determine whether oral intake of an extended release (R)-Silodosin formulation, when administered with food, results in a reduced effect on aspermia or azoospermia.

A double-blind, placebo controlled study is conducted over a two week period. A total of 12 subjects, aged 20-45 years, are chosen for the study. An initial analysis of each subject's semen collected via masturbation after 3 days of abstinence by microscopic examination of the fresh semen. Each subject receives two successive single doses of 12 mg extended release (R)-Silodosin, one in fed condition, the other in fasted condition.

A semen analysis of each subject is conducted utilizing the methods described above at thirty or forty-eight hours after the administration of each dose.

Administration of the extended release (R)-Silodosin formulation led to aspermia or azoospermia in 100% of the twelve male subjects in both fed and fasted conditions.

Without further elaboration, it is believed that one skilled in the art, using the preceding description, can utilize the present invention to the fullest extent. The following examples are illustrative only, and not limiting of the remainder of the disclosure in any way whatsoever.

While specific embodiments of the present invention have been described, other and further modifications and changes may be made without departing from the spirit of the invention. All further and other modifications and changes are included that come within the scope of the invention as set forth in the claims. The disclosure of each publication cited above is expressly incorporated by reference in its entirety to the same extent as if each were incorporated by reference individually.

Example 7

(R)-Silodosin Pharmacokinetic Properties

The pharmacokinetic properties of (R)-Silodosin (SIL) is modeled based on plasma concentration-versus-time profiles obtained after a single administration of 8 mg of (R)-Silodosin to healthy volunteers. (R)-Silodosin data are described by a bi-compartment model with a first-order input rate constant. The pharmacokinetic properties of (R)-Silodosin were measured on the basis of observed plasma concentrations. The observed plasma concentrations validate the plasma concentration simulation methods for (R)-Silodosin.

Since the pharmacokinetic properties of (R)-Silodosin are linear over the dose-range 1-24 mg and are time-independent, the models are suitable for predicting the pharmacokinetic profiles of the compounds given at different doses under multiple dosing regimens.

A contraception is maintained up to 24 h after the administration of a 12-mg single dose of (R)-Silodosin. The C24 is the (R)-Silodosin plasma concentration 24 hours postdose. Thus, a dosing regimen maintaining (R)-Silodosin plasma concentrations significantly above C24 results in a continuous contraception.

Maintaining the (R)-Silodosin concentration at a level at least equal to C24 should be sufficient; however, due to the variability of the pharmacokinetic properties of (R)-Silodosin and the individual metabolism variability, it is important to provide a significant security margin (ie., minimum (R)-Silodosin concentration significantly higher than C24).

Example 8

Effective Exposure after Repeated Administrations of (R)-Silodosin

Figure 2:
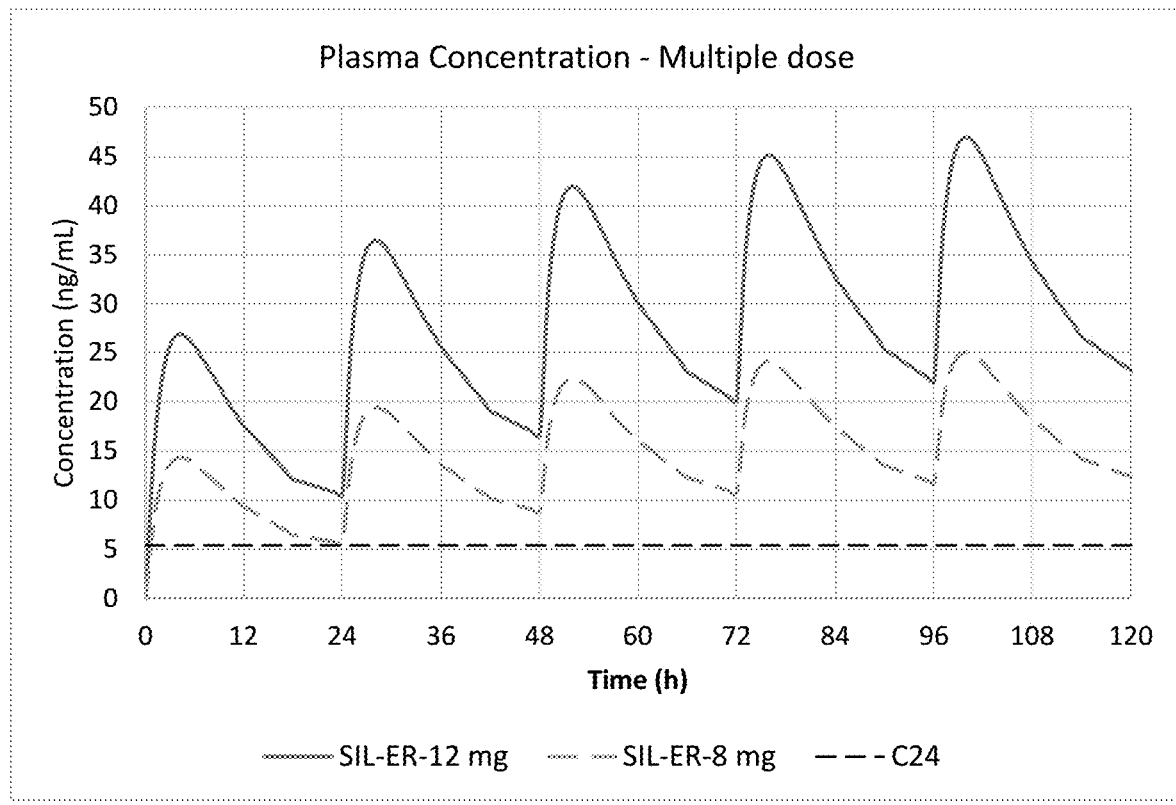
FIG. 2 is a graph illustrating plasma concentration-versus-time profiles for (R)-Silodosin after multiple daily oral administrations of extended release formulations of 12 or 8 mg of (R)-Silodosin. The plasma concentration obtained 24 h after a single administration of 8 mg of (R)-Silodosin in an immediate release formulation (C24) is also presented in the graph.

The model is used to simulate the pharmacokinetic properties of (R)-Silodosin after at least two to at least five daily administrations of 8 mg of (R)-Silodosin. After the administration of the (R)-Silodosin formulation A, the (R)-Silodosin plasma concentrations are constantly above C24, as presented in FIG. 2.

The effective exposure of (R)-Silodosin concentration is significantly superior to the C24 concentration as for the second administration, showing that the contraceptive efficiency is maintained.

Furthermore, the maximal plasma concentration ($C_{max}$) is inferior to the $C_{max}$ measured past the administration of immediate release 8 mg (R)-Silodosin formulations where the risk of orthostatic hypotension is considered acceptable by health authorities.

Thus, the administration of (R)-Silodosin formulation A reduces the risk of unacceptable orthostatic hypotension.

Example 9

Delayed or Omitted Intake does not Affect Contraceptive Effect

The administration of 8 and 12 mg (R)-Silodosin extended release formulations according to formulation A allows maintaining the contraception all along the once daily treatment, including in case of delayed intake and in case of a single omission.

Figure 3:
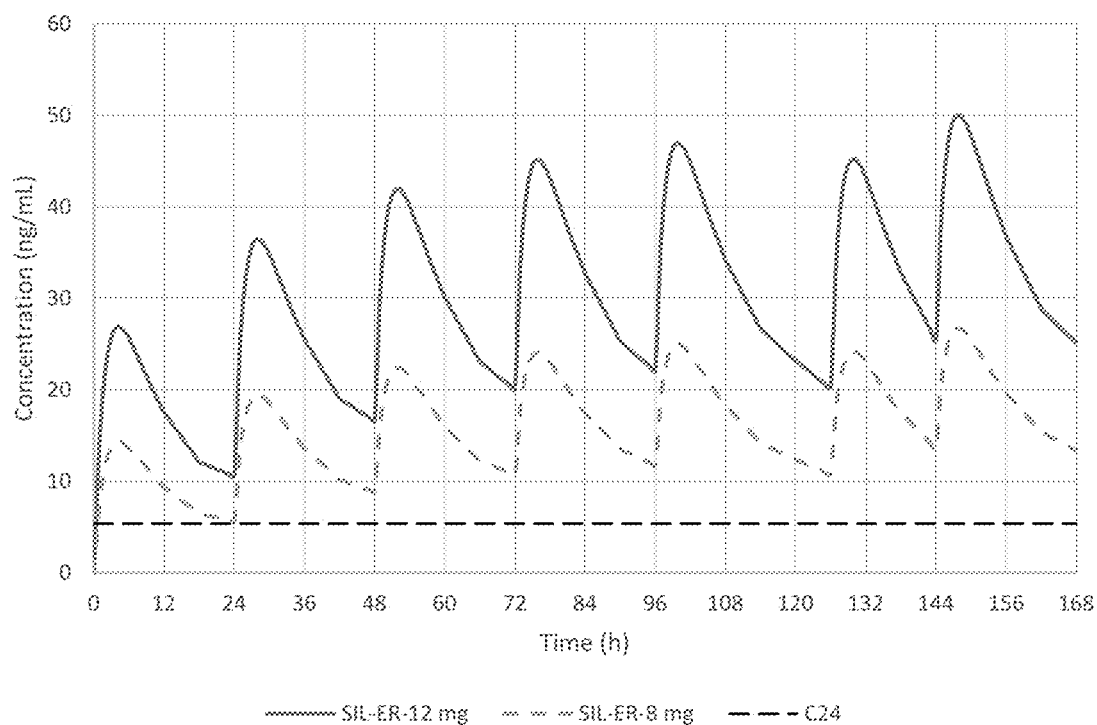
FIG. 3 is a graph illustrating plasma concentration-versus-time profile for (R)-Silodosin after multiple daily oral administrations of 12 or 8 mg of (R)-Silodosin extended release formulation (ER) and a 6-hour delayed $6^{th}$ intake. The plasma concentration obtained 24 h after a single administration of 8 mg of (R)-Silodosin in an immediate release formulation (C24) is also presented in the graph.

A 6-hour delay in the 6th intake (intake at 126 hours instead of 120 hours) does not allow the (R)-Silodosin concentration to drop below the C24 concentration, as illustrated in FIG. 3.

Figure 4:
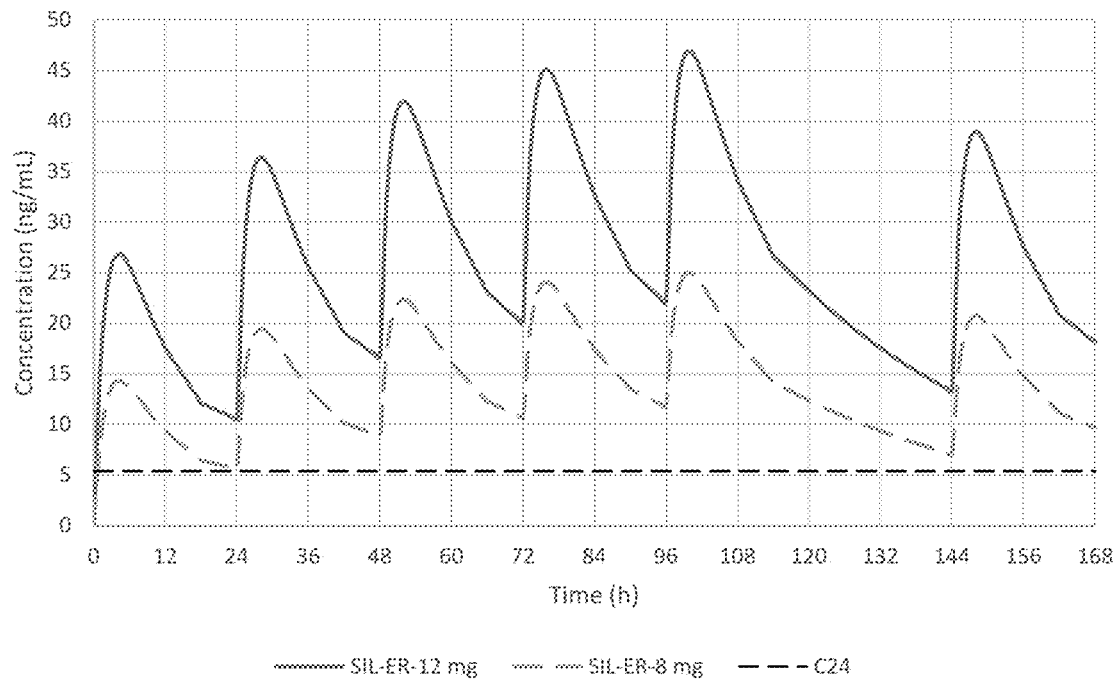
FIG. 4 is a graph illustrating plasma concentration-versus-time profile for (R)-Silodosin after multiple daily oral administrations of 12 or 8 mg of (R)-Silodosin extended release formulation (ER) and an omitted $6^{th}$ intake. The plasma concentration obtained 24 h after a single administration of 8 mg of (R)-Silodosin in an immediate release formulation (C24) is also presented in the graph.

Furthermore, the (R)-Silodosin plasma concentration is maintained above C24 even if the 6th day administration is omitted, as illustrated in FIG. 4.

Thus, as confirmed by the results presented in FIG. 3 and FIG. 4, the administration according to the present invention is able to maintain the contraception all along the treatment duration, including in case of delayed or omitted intake.

The invention claimed is:

1. A method for reversible, continuous non-hormonal contraception in a male subject, the method comprising administering once daily at about the same time, an oral dose of a composition comprising:
   (i) an extended release formulation of (R)-silodosin in an amount effective, when administered once daily at about the same time, to induce a reversible condition of aspermia, azoospermia or severe oligozoospermia sufficient for contraceptive effect in the male subject; and
   (ii) a pharmaceutically acceptable carrier,
   wherein once daily administration of the formulation at about the same time provides a reversible contraceptive effect, but does not affect the quality of orgasm in the male subject.

2. The method of claim 1, wherein the quality of orgasm is measured on the Numerical Rating Scale for subjective quality of orgasm.

3. The method of claim 1, wherein the amount of (R)-silodosin in the composition administered once daily at about the same time is about 4 to about 12 mg.

4. The method of claim 1, wherein the amount of (R)-silodosin in the composition administered once daily at about the same time is about 8 mg.

5. A method for reversible, continuous non-hormonal contraception in a male subject, the method comprising administering once daily at about the same time, an oral dose of a composition comprising:
- (i) an extended release formulation of (R)-silodosin in an amount effective, when administered once daily at about the same time, to induce a reversible condition of aspermia, azoospermia or severe oligozoospermia sufficient for contraceptive effect in the male subject; and
- (ii) a pharmaceutically acceptable carrier,
- wherein once daily administration of the formulation at about the same time provides a reversible contraceptive effect, but does not cause discomfort upon ejaculation in the male subject.

6. The method of claim 5, wherein the amount of (R)-silodosin in the composition administered once daily at about the same time is about 4 to about 12 mg.

7. The method of claim 5, wherein the amount of (R)-silodosin in the composition administered once daily at about the same time is about 8 mg.

8. A method for reversible, continuous non-hormonal contraception in a male subject, the method comprising administering once daily at about the same time, an oral dose of a composition comprising:
- (i) an extended release formulation of (R)-silodosin in an amount effective, when administered once daily at about the same time, to induce a reversible condition of aspermia, azoospermia or severe oligozoospermia sufficient for contraceptive effect in the male subject; and
- (ii) a pharmaceutically acceptable carrier,
- wherein a delay in administering one daily dose after an initial period of at least two consecutive days with doses administered at about the same time does not affect the contraceptive effect in the male subject, wherein the delay does not exceed 2, 4, 6, 8, 10 12, 16, 20 or 24 hours from the day-before intake time.

9. The method of claim 8, wherein the initial period of consecutive days is at least 5 days.

10. The method of claim 8, wherein the amount of (R)-silodosin in the composition administered once daily at about the same time is about 4 to about 12 mg.

11. The method of claim 8, wherein the amount of (R)-silodosin in the composition administered once daily at about the same time is about 8 mg.

12. The method of claim 8, wherein the delay in administering one daily dose does not exceed 4 hours.

13. The method of claim 8, wherein the delay in administering one daily dose does not exceed 6 hours.

14. The method of claim 8, wherein the delay in administering one daily dose does not exceed 8 hours.

15. The method of claim 8, wherein the delay in administering one daily dose does not exceed 10 hours.

16. The method of claim 8, wherein the delay in administering one daily dose does not exceed 12 hours.

* * * * *